(12) United States Patent
DiSpirito et al.

(10) Patent No.: US 6,489,156 B1
(45) Date of Patent: Dec. 3, 2002

(54) RHODOBACTER STRAIN FOR ODOR REMEDIATION OF ANAEROBIC LIVESTOCK WASTE LAGOONS AND BIOMASS PRODUCTION

(75) Inventors: Alan A. DiSpirito; Young S. Do; Gregory J. Phillips; James A. Zahn, all of Ames, IA (US)

(73) Assignee: Iowa State University Research Foundation, Inc., Ames, IA (US)

(*) Notice: Subject to any disclaimer, the term of this patent is extended or adjusted under 35 U.S.C. 154(b) by 0 days.

(21) Appl. No.: 09/565,063

(22) Filed: May 5, 2000

Related U.S. Application Data

(60) Provisional application No. 60/133,087, filed on May 7, 1999.

(51) Int. Cl.[7] .............................. C12N 1/00; C12N 1/04; B09B 3/00; C07G 17/00
(52) U.S. Cl. .................. 435/243; 435/260; 435/262; 435/262.5; 435/267; 435/268; 435/289.1; 435/307.1; 435/801; 435/821
(58) Field of Search ................. 435/243, 260, 435/262, 262.5, 264, 267, 289.1, 801, 821 252.1, 252.3

(56) References Cited

U.S. PATENT DOCUMENTS 5,736,049 A   4/1998  Bundy et al. ............... 210/620
5,744,041 A   4/1998  Grove ........................ 210/602
5,861,096 A   1/1999  Mason et al. ............... 210/631

FOREIGN PATENT DOCUMENTS

JP          03147726 A2 *   6/1991

OTHER PUBLICATIONS

Sasaki et al. 1996, Mizu Kankyo Gakkaishi, vol. 19(1):63–70.*

Do et al. Abstract Q–7, General Meeting of Am. Soc. for Microbiol. Atlanta, GA, May 17–21, 1998.*

Michiharu Kobayashi, et al.—"Waste Remediation and Treatment Using Anoxygenic Phototrophic Bacteria", Chapter 62, Anoxygenic Photosynthetic Bacteria, pp. 1269–1282, 1995.

* cited by examiner

*Primary Examiner*—Rebecca E. Prouty
*Assistant Examiner*—Manjunath Rao
(74) *Attorney, Agent, or Firm*—Dickstein Shapiro Morin & Oshinsky LLP

(57) ABSTRACT

A Rhodobacter species and variants thereof are provided for odor remediation of anaerobic livestock waste lagoons. Also provided are vector systems and genetically reconstituted Rhodobacter PS9 cells, and related methods for biomass production in anaerobic livestock waste lagoons.

16 Claims, 20 Drawing Sheets

LOCUS    PS9.con    1419 bp    DNA    17-APR-1998ORIGIN

```
   1 AATGAACGCT GGCGGCAGGC CTAACACATG CAAGTCGAGC GAAGTCTTCG GACTTAGCGG
  61 CGGACGGGTG AGTAACGCGT GGGAACATGC CCAAAGGTAC GGAATAGCCC CGGGAAACTG
 121 GGAGTAATAC CGTATGTGCC CTTCGGGGGA AAGATTTATC GCCTTTGGAT TGGCCCGCGT
 181 TGGATTAGGT AGTTGGTGGG GTAATGGCCT ACCAAGCCGA CGATCCATAG CTGGTTTGAG
 241 AGGATGATCA GCCACACTGG GACTGAGACA CGGCCCAGAC TCCTACGGGA GGCAGCAGTG
 301 GGGAATCTTA GACAATGGGC GCAAGCCTGA TCTAGCCATG CCGCGTGATC GATGAAGGCC
 361 TTAGGGTTGT AAAGATCTTT CAGGTGGGAA GATAATGACG GTACCACCAG AAGAAGCCCC
 421 GGCTAACTCC GTGCCAGCAG CCGCGGTAAT ACGGAGGGGG CTAGCGTTAT TCGGAATTAC
 481 TGGGCGTAAA GCGCACGTAG GCGGACTGGA AAGTCAGGGG TGAAATCCCG GGCTCAACC
 541 CCGGAACTGC CTTTGAAACT CCCAGTCTTG AGGTCGAGAG AGGTGAGTGG AATTCCGAGT
 601 GTAGAGGTGA AATTCGTAGA TATTCGGAGG AACACCAGTG GCGAAGGCGG CTCACTGGCT
 661 CGATACTGAC GCTGAGGTGC GAAAGCGTGG GGAGCAAACA GGATTAGATA CCCTGGTAGT
 721 CCACGCCGTA AACGATGAAT GCCAGTCGTC GGGCAGCATG CTGTTCGGTG ACACACCTAA
 781 CGGATTAAGC ATTCCGCCTG GGGAGTACGG CCGCAAGGTT AAAACTCAAA GGAATTGACG
 841 GGGCCCGCA CAAGCGGTGG AGCATGTGGT TTAATTCGAA GCAACGCGCA GAACCTTACC
 901 AACCCTTGAC ATGGCGATCG CGGTTCCAGA GATGGTTCCT TCAGTTCGGC TGGATCGCAC
 961 ACAGGTGCTG CATGGCTGTC GTCAGCTCGT GTCGTGAGAT GTTCGGTTAA GTCCGGCAAC
1021 GAGCGCAACC CACGTCCTCA GTTGCCAGCA TTCAGTTGGG CACTCTGGGG AAACTGCCGG
1081 TGATAAGCCG GAGGAAGGTG TGGATGACGT CAAGTCCTCA TGGCCCTTAC GGGTTGGGCT
1141 ACACACGTGC TACAATGGCA GTGACAATGG GTTAATCCCA AAAAGCTGTC TCAGTTCGGA
1201 TTGGGGTCTG CAACTCGACC CCATGAAGTC GGAATCGCTA GTAATCGCGT AACAGCATGA
1261 CGCGGTGAAT ACGTTCCCGG GCCTTGTACA CACCGCCCGT CACACCATGG GAATTGGTTC
1321 TACCCGAAGG CGGTGCGCCA ACCTCGCAAG AGGAGGCAGC CGACCACGGT AGGATCAGTG
1381 ACTGGGGTGA AGTCGTAACA AGGTAGCCGT AGGGGAACC//
```

FIG.9

16S rRNA OLIGONUCLEOTIDE PROBES

| | GENERA/GROUP | PROBE | SEQUENCE | WASH TEMP (C) |
|---|---|---|---|---|
| (a) | *Rhodobacter PS9* | Rhodo 2 | ACCATCTCTGGAACCGCG | 45 |
| (b) | Eubacteria | EUB338 | GCTGCCTCCCGTAGGAGT | 45 |
| (c) | Archaraea | | GTGCTCCCCCGCCAATTCCT | 56 |
| (d) | Eucaryote | | GGGCATCACAGACCTG | 40 |
| (e) | Universal | | ACGGGGGGTGTGTRC | 45 |

FIG.15

SEQUENCE LISTING

<160> NUMBER OF SEQ ID NOS: 6

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence: Oligonucleotide probe

<400> SEQUENCE: 1

```
accatctctg gaaccgcg                                                  18
```

<210> SEQ ID NO 2
<211> LENGTH: 1419
<212> TYPE: DNA
<213> ORGANISM: Rhodobacter sp.
<220> FEATURE:
<223> OTHER INFORMATION: 16S rDNA of RPS9

<400> SEQUENCE: 2

```
aatgaacgct ggcggcaggc ctaacacatg caagtcgagc gaagtcttcg gacttagcgg      60
cggacgggtg agtaacgcgt gggaacatgc ccaaaggtac ggaatagccc cgggaaactg     120
ggagtaatac cgtatgtgcc cttcggggga aagatttatc gcctttggat tggcccgcgt     180
tggattaggt agttggtggg gtaatggcct accaagccga cgatccatag ctggtttgag     240
aggatgatca gccacactgg gactgagaca cggcccagac tcctacggga ggcagcagtg     300
gggaatctta gacaatgggc gcaagcctga tctagccatg ccgcgtgatc gatgaaggcc     360
ttagggttgt aaagatcttt caggtgggaa gataatgacg gtaccaccag aagaagcccc     420
ggctaactcc gtgccagcag ccgcggtaat acggaggggg ctagcgttat tcggaattac     480
tgggcgtaaa gcgcacgtag gcggactgga aagtcagggg tgaaatcccg gggctcaacc     540
ccggaactgc ctttgaaact cccagtcttg aggtcgagag aggtgagtgg aattccgagt     600
gtagaggtga aattcgtaga tattcggagg aacaccagtg gcgaaggcgg ctcactggct     660
cgatactgac gctgaggtgc gaaagcgtgg ggagcaaaca ggattagata ccctggtagt     720
ccacgccgta aacgatgaat gccagtcgtc gggcagcatg ctgttcggtg acacacctaa     780
cggattaagc attccgcctg gggagtacgg ccgcaaggtt aaaactcaaa ggaattgacg     840
ggggcccgca caagcggtgg agcatgtggt ttaattcgaa gcaacgcgca gaaccttacc     900
```

```
aacccttgac atggcgatcg cggttccaga gatggttcct tcagttcggc tggatcgcac      960
acaggtgctg catggctgtc gtcagctcgt gtcgtgagat gttcggttaa gtccggcaac     1020
gagcgcaacc cacgtcctca gttgccagca ttcagttggg cactctgggg aaactgccgg     1080
tgataagccg gaggaaggtg tggatgacgt caagtcctca tggcccttac gggttgggct     1140
acacacgtgc tacaatggca gtgacaatgg gttaatccca aaaagctgtc tcagttcgga     1200
ttggggtctg caactcgacc ccatgaagtc ggaatcgcta gtaatcgcgt aacagcatga     1260
cgcggtgaat acgttcccgg gccttgtaca caccgcccgt cacaccatgg gaattggttc     1320
tacccgaagg cggtgcgcca acctcgcaag aggaggcagc cgaccacggt aggatcagtg     1380
actggggtga agtcgtaaca aggtagccgt aggggaacc                            1419
```

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence:
      Oligonucleotide probe

<400> SEQUENCE: 3
gctgcctccc gtaggagt                                                     18

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence:
      Oligonucleotide probe

<400> SEQUENCE: 4
gtgctccccc gcaattcct                                                    19

<210> SEQ ID NO 5
<211> LENGTH: 16
<212> TYPE: DNA
<213> ORGANISM: Artificial Sequence
<220> FEATURE:
<223> OTHER INFORMATION: Description of Artificial Sequence:
      Oligonucleotide probe

<400> SEQUENCE: 5
gggcatcaca gacctg                                                       16

<210> SEQ ID NO 6
<211> LENGTH: 15
<212> TYPE: DNA
<213> ORGANISM: Artificial Sequence
<220> FEATURE:
<223> OTHER INFORMATION: Description of Artificial Sequence:
      Oligonucleotide probe

<400> SEQUENCE: 6 acgggggtg tgtrc                                                         15

RHODOBACTER STRAIN FOR ODOR REMEDIATION OF ANAEROBIC LIVESTOCK WASTE LAGOONS AND BIOMASS PRODUCTION

This application claims priority to U.S. Provisional Patent Application No. 60/133,087 filed on May 7, 1999 which is hereby incorporated by reference in its entirety.

FIELD OF THE INVENTION

This invention relates generally to the isolation and use of bacterial strains for odor remediation and fermentation in anaerobic livestock waste lagoons. In particular, the invention relates to the isolation of a biologically pure culture of a Rhodobacter PS9 ("RPS9") bacterial strain and methods of using the bacterial strain to reduce the concentration of malodorous volatile organic compounds in anaerobic livestock waste lagoons and for biomass production from genetically reconstituted RPS9 cells.

REFERENCES

Several publications are referenced herein. Full citations for these publications are provided below. The disclosures of these publications are hereby incorporated herein by reference in their entirety, unless otherwise noted.

BACKGROUND OF THE INVENTION

Livestock waste lagoons are large reservoirs used for the storage and treatment of livestock waste and runoff. In order to operate efficiently, the waste must be loaded at an appropriate rate and maintained at a minimum volume. Such lagoons may be aerobic, anaerobic or facultative. While aerobic waste lagoons control sludge and odor better than anaerobic lagoons, they require the use of mechanical aerators to ensure adequate oxygen. In contrast, anaerobic lagoons can treat high waste load rates, do not require aeration, and thus operate at a much lower cost.

Anaerobic lagoons are often associated with noxious odors causing environmental problems associated with their use. In addition, the proximity of waste lagoons to populated areas exposes waste lagoon operators to nuisance lawsuits and potential liability. To help reduce problems associated with noxious odors, a two-stage anaerobic lagoon may be employed, wherein treated waste from a first cell is transferred to a second adjacent cell. However, operation of a two-stage lagoon is expensive. The main source of odors associated with anaerobic a waste lagoons results from the anaerobic digestion of complex, volatile, organic compounds resulting in the production of malodorous volatile organic and inorganic compounds.

U.S. Pat. No. 5,861,096 is directed to reducing odors from wastewater by chemical treatment. According to the patent, the most common source of odors in wastewater is reduced sulfur compounds resulting from anaerobic bacterial decomposition of biodegradable organic matter in the presence of sulfates. The patent refers to spraying an aqueous solution of a chlorine compound over the surface of a wastewater lagoon to react with the sulfides emanating from the surface. The spray may be provided through spray nozzles using a pipe distribution system and must cover at least 1,000 square feet.

U.S. Pat. No. 5,744,041 is directed to adding undefined cultures of anaerobic bacteria to wastewater to reduce the biological oxygen demand (BOD) of the wastewater. A portion of the treated wastewater with a reduced BOD is mixed with aerobic bacteria to form a liquor comprising water and aerobic organisms. The liquor is subjected to microzone treatment to remove a portion of the aerobic microorganisms. "Genetically engineered" or "genetically reconstituted" organisms are often used for large-scale biomass production. Typically, a gene encoding a protein of interest is cloned into a bacteria using a vector system. The bacteria are grown in a large-scale fermentation process and induced to express the protein of interest which is then isolated from the bacterial cells. Significant costs are associated with establishing and maintaining particular bacterial growth conditions, including providing the appropriate growth media, temperature, pH, and oxygen level. Most plasmid vector systems rely upon use of antibiotic selection genes to maintain the presence of the vector in the cell. Furthermore, vector systems typically require the addition of exogenous compounds to induce expression of genes under the control of promoter sequences.

What is needed are new methods of reducing the odors associated with livestock waste lagoons in a reproducible, cost-effective and environmentally friendly manner. Systems and methods for large-scale biomass production are also needed that rely on naturally-occurring conditions and do not require the addition of antibiotics or other exogenous compounds.

SUMMARY OF THE INVENTION

This invention provides a newly isolated Rhodobacter PS9 strain and methods of using such strain to reduce the odor associated with livestock waste lagoons. Also provided herein are methods of using genetically reconstituted Rhodobacter PS9 cells for large-scale biomass/enzyme production.

The present inventors have identified RPS9 as the major photosynthetic bacterium in certain anaerobic livestock waste lagoons. In these photosynthetic lagoons, this bacterium constitutes 40 to 60% of the total microbial populations. The present invention provides a newly isolated photosynthetic bacterial strain, RPS9. Cultures of RPS9 are used, according to a preferred embodiment of the invention, to inoculate malodorous livestock waste lagoons and reduce odor through degradation of various volatile organic compounds.

In one preferred embodiment of the invention, a biologically pure culture of bacteria having some or all of the identifying characteristics of RPS9 is provided. In this embodiment, the identifying characteristics of RPS9 may include a bacteriochlorophyll α ("Bchl") profile, a cell extract absorption spectra, a MIDI-FAME (Microbial Identification System-Fatty Acid Methyl Ester) profile, and a species specific rRNA profile. The biologically pure culture bacteria is preferably capable of degrading malodorous volatile organic compounds such as fatty acids (e.g., butanoic acid, pentanoic acid, hexanoic acid, and heptanoic acid) and aromatic compounds (e.g., phenol, para-cresol, and 3-methyl-indole).

In another preferred embodiment, a method of inducing the growth of RPS9 and variants thereof in a livestock waste lagoon is provided by controlling lagoon conditions such as pH, temperature, and organic load. Growth is enhanced by adjusting the temperature to at least at about 22° C. or above, the pH to about pH 6.9 to about 7.8, and the organic load to a protein concentration of about 1 g per liter and, preferably, a dry weight below about 4 g per liter.

In another preferred embodiment, an inoculum comprising a biologically pure culture of RPS9 or variant thereof and a suitable carrier is provided. The inoculum is used to inoculate a livestock waste lagoon. The inoculum is typically used to inoculate a livestock waste lagoon by providing from about 1 ml to about 5 ml of the bacterium (at a concentration of about 2 mg cell protein/ml) to the lagoon by any suitable method, preferably after adjusting the temperature, pH and organic load of the livestock waste lagoon.

In a further preferred embodiment, a method of genetically reconstituting a RPS9 strain is provided by introducing a vector comprising a gene encoding a protein product, a promoter to control expression of the protein product, and a selection gene. Preferably, the vector system does not require the continual presence of antibiotics to maintain the vector in the RPS9 strain. The promoter preferably does not require the addition of a substrate to induce expression of the protein product. The selection gene is preferably a gene essential to the survival of the RPS9 strain. A particularly preferred selection gene is the ffh gene. Reece, K. R and Phillips, G. J. (1995); Phillips, G. J. and T. J. Silhavy (1992). The gene may be inserted into the vector using any suitable recombinant DNA technique or method. The vector may be introduced into the RPS9 strain using any suitable technique or method.

In a yet another preferred embodiment, a fermentation system and method for producing a protein is provided. A genetically reconstituted RPS9 strain or variant thereof is grown in a livestock waste lagoon. The RPS9 cells are preferably separated from the liquid waste and induced to express a protein product in an inducing media. The protein product is preferably separated from the induced RPS9 cells. The fermentation system and method provides significant cost savings advantages over standard fermentation methods since the RPS9 are grown in waste products and do not require addition of antibiotics to maintain vectors, or exogenous compounds to induce expression of the protein product.

Additional embodiments and advantages of the present invention will be set forth in part in the description that follows, and in part will be obvious from the description, or may be learned through the practice of the invention. The objects and advantages of the invention will be attained by means of the instrumentalities and combinations particularly pointed out in the appended claims.

BRIEF DESCRIPTION OF THE DRAWINGS

FIG. 9 shows the primary structure of the 16S rDNA of RPS9 (SEQ ID NO: 2).

FIG. 13D shows composite Volatile Fatty Acid, Aromatics and Bchl profiles from anaerobic livestock waste lagoons over an eight-month period. FIG. 13E shows composite phenolics and Bchl profiles from anaerobic livestock waste lagoons over an eight-month period.

FIG. 15 shows the sequence of the 16S rRNA oligonucleotide probes (SEQ ID NOS 1, 3-6, respectively, in order of appearance) used to identify the 16S rDNA of RPS9 (a) and other bacteria (b–e).

DETAILED DESCRIPTION OF PREFERRED EMBODIMENTS

Reference will now be made in detail to the presently preferred embodiments of the invention, which together with the following examples, serve to explain the principles of the invention.

Figure 1:
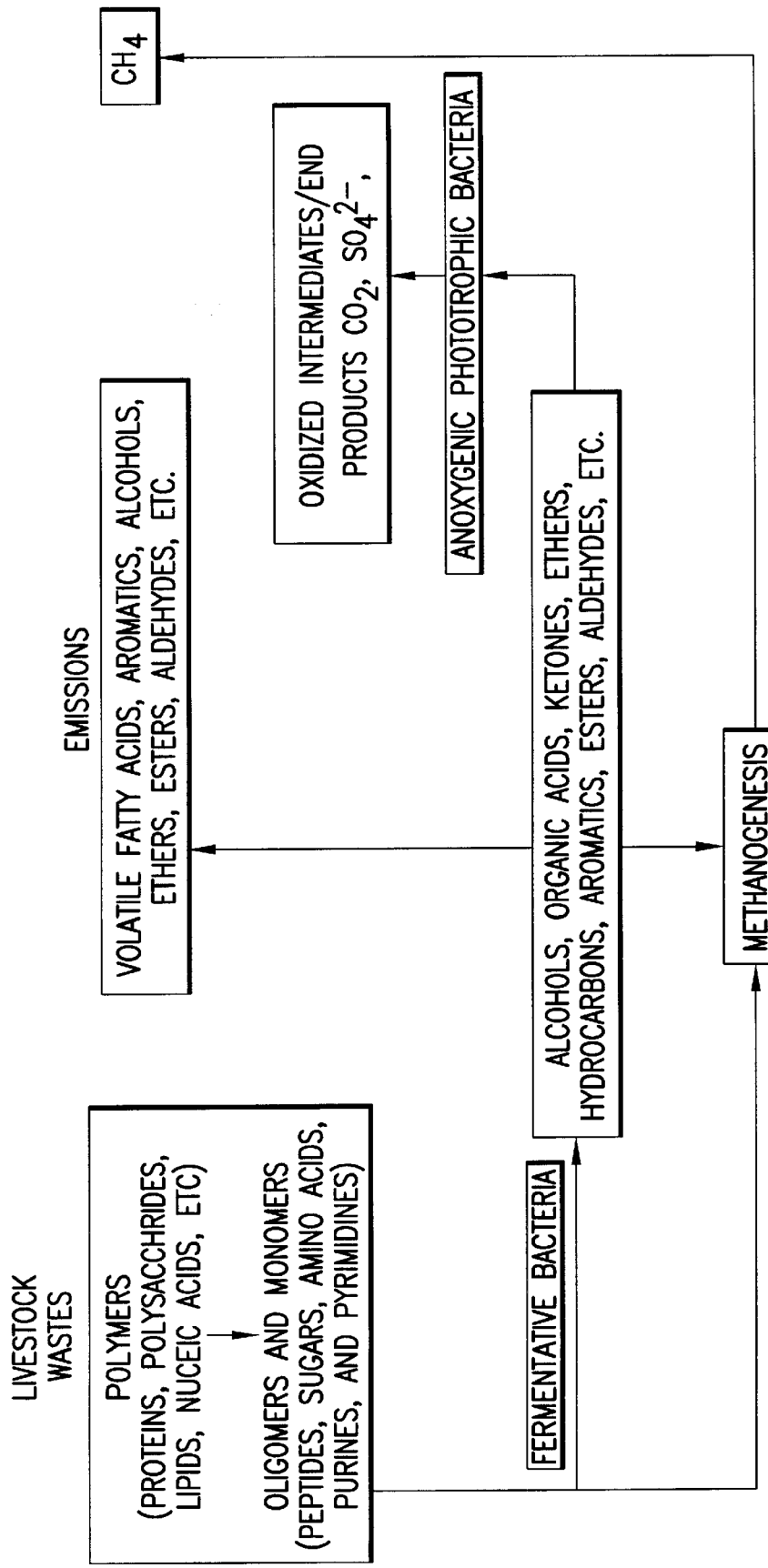
FIG. 1 shows the steps in the microbial degradation of livestock wastes under anaerobic conditions.
Figure 2:
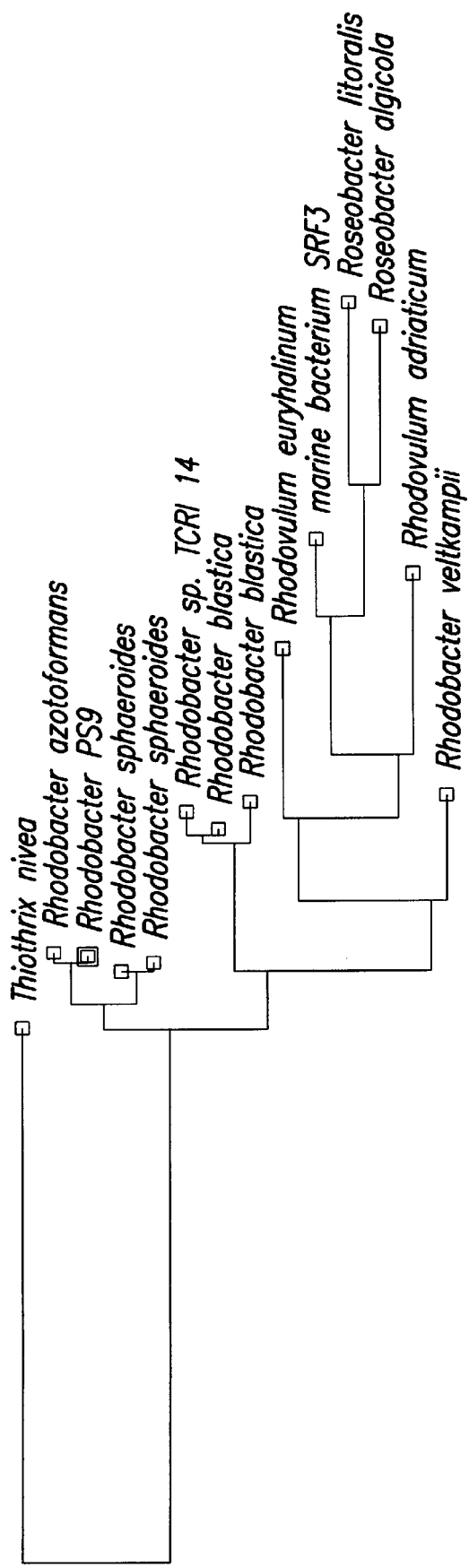
FIG. 2 is a distance matrix tree showing phylogenetic relationships between RPS9 and phototrophic and nonphototrophic relatives. The scale bar represents 10% nucleotide substitution per 100 nucleotides.

Odor production in livestock waste results from the interaction of several microbial consortiums. One such consortium is found between fermentative microorganisms and photosynthetic bacteria. Fermentative microorganisms degrade complex macronutrients into low molecular weight organic compounds, such as volatile fatty acids, aromatic compounds such as phenols, cresols and indoles, and produce molecular hydrogen. Photosynthetic bacteria utilize the end products of the fermentative microorganisms as substrates to produce bacterial cells and carbon dioxide. (FIGS. 1 and 2).

Photosynthetic bacteria carry out anoxygenic or anaerobic photosynthesis. Anoxygenic photosynthesis relies upon exogenous substrates such as hydrogen sulfide, hydrogen, organic compounds such as volatile fatty acids, and aromatic compounds to provide reducing agents, as opposed to oxygenic photosynthesis which employs $H_2O$ as a reducing agent. Purple and green photosynthetic bacteria are found in high concentration in uncovered natural or livestock waste lagoons, especially in warm weather. Several investigators have reported temporal changes in the pigmentation of the lagoons from pink to rose to brown, color changes that correlate with changes in temperature and pH. Anaerobic processing of livestock waste results in the production of malodorous products such as hydrogen sulfide, ammonia, and volatile organic compounds (DiSpirito et al., 1995; 1996, Do et al., 1998, 1999, Mackie et al. 1998, Miner, 1982; 1995).

One commonly observed microbial event in anaerobic swine waste lagoons is the development of purple color and reduction of odor in early summer. The color change is the result of a bloom in the population of photosynthetic bacteria (DiSpirito et al., 1995; 1996, Do et al., 1998, 1999, Zahn et al., 2000a, 2000b, 2000c). In these systems the photosynthetic bacterial utilizes the end products of fermentative bacteria as carbon and electron sources (FIG. 1). The end product of this consortium is the degradation of organic matter into bacterial cells and $CO_2$. In this system, the photosynthetic reaction center replaces the terminal electron acceptor as the electron sink allowing more complete degradation of organic wastes.

Figure 5:
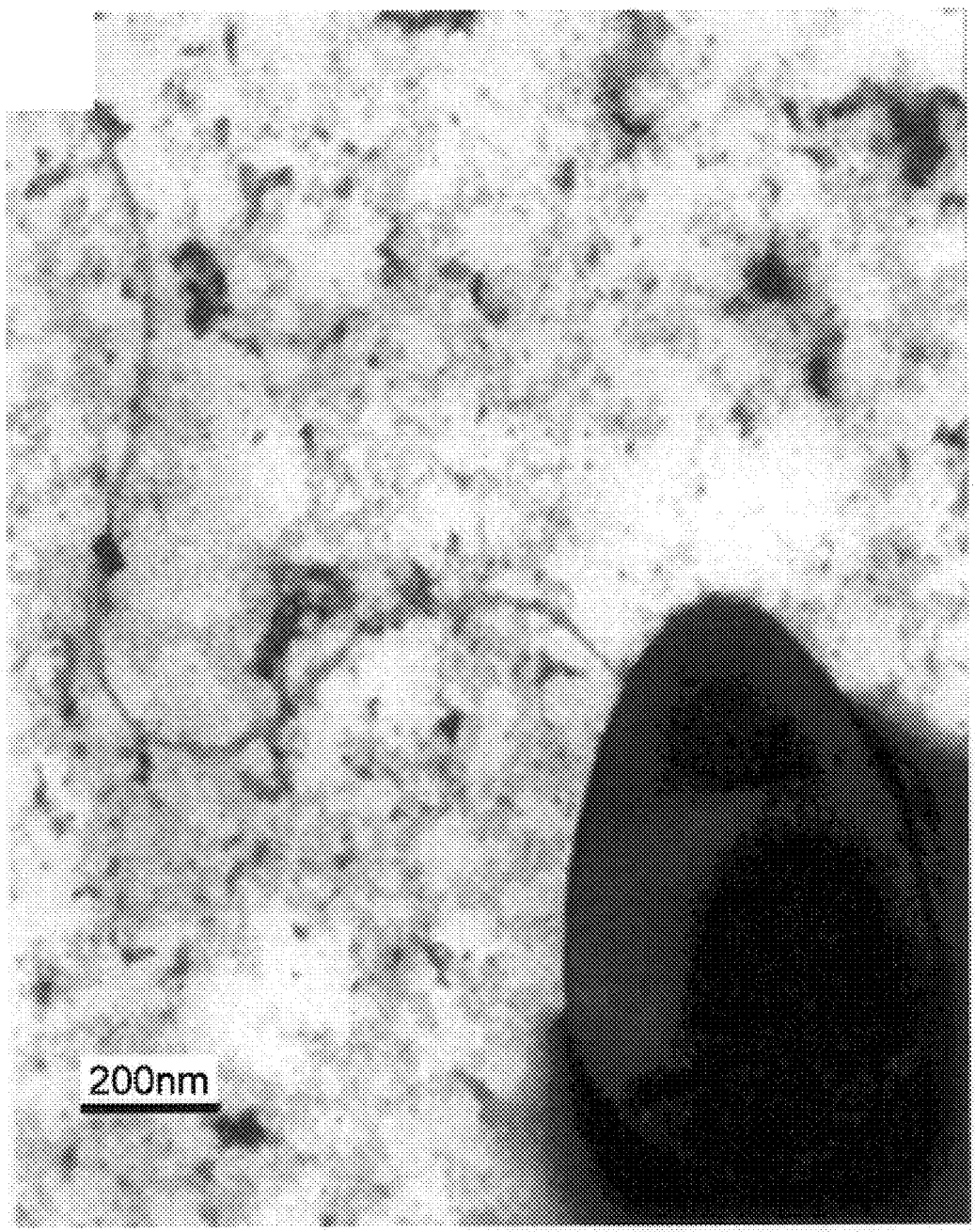
FIG. 5 is an electron micrograph of a RPS9 cell negatively stained with 2% aqueous uranyl acetate.
Figure 7:
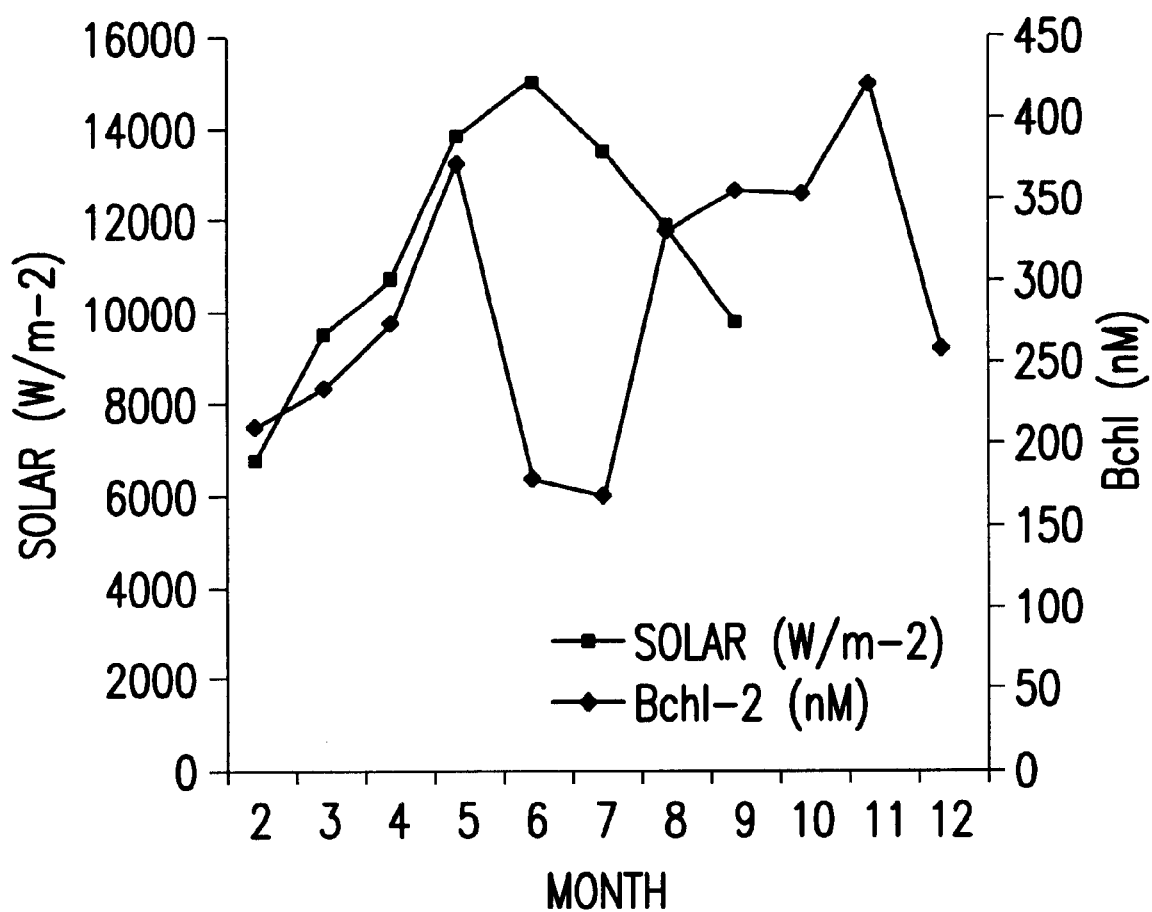
FIG. 7 shows the changes in bacteriochlorophyll in relation to solar radiation in an anaerobic livestock waste lagoons.
Figure 8A:
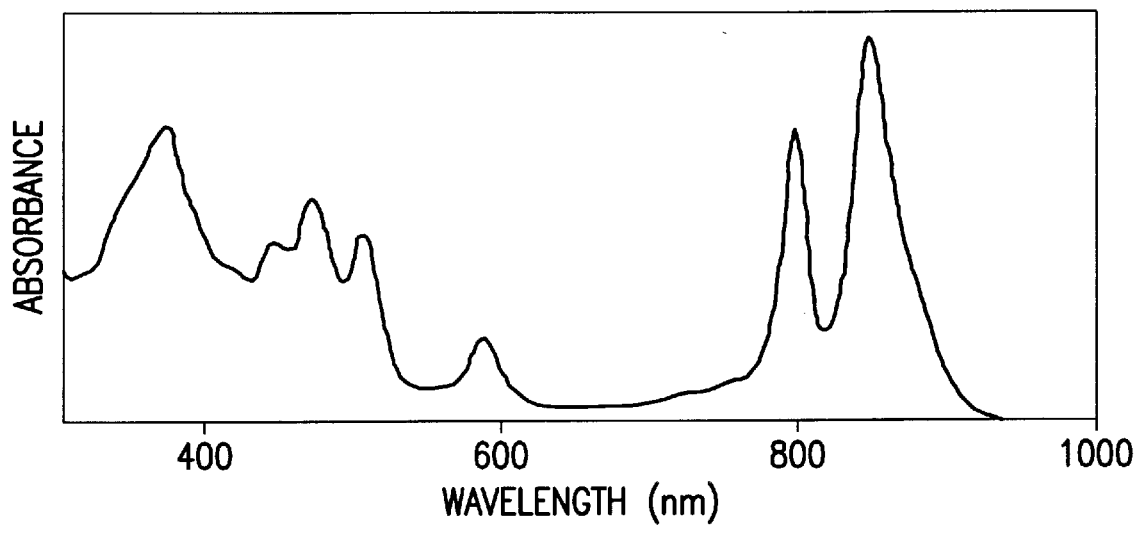
FIGS. 8(a,b) shows the absorption spectra of cell extracts of a. *Rhodobacter azotoformans* (Hirisishi et al., 1995) and b. RPS9.
Figure 8B:
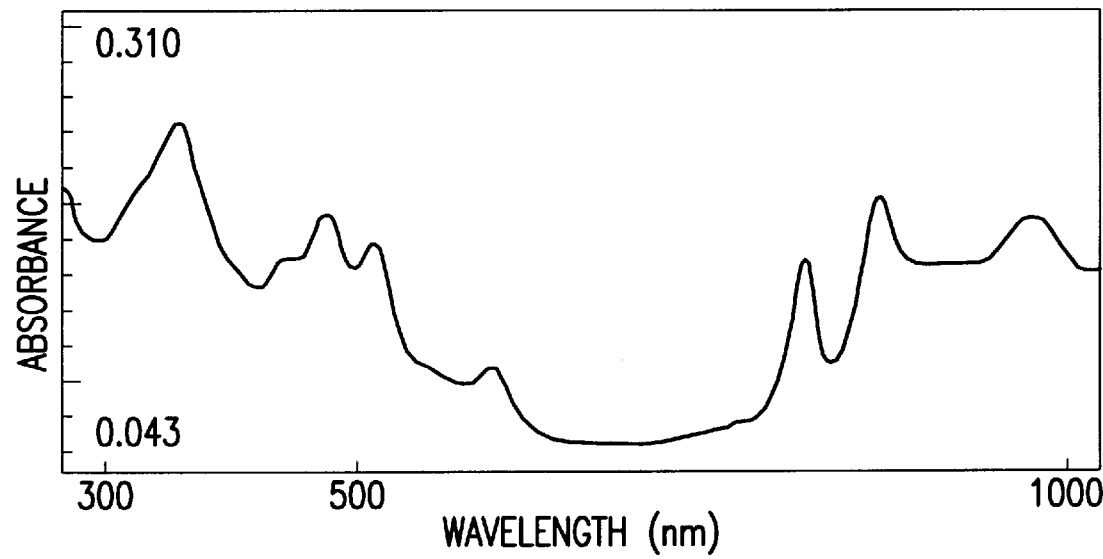
Figure 10:
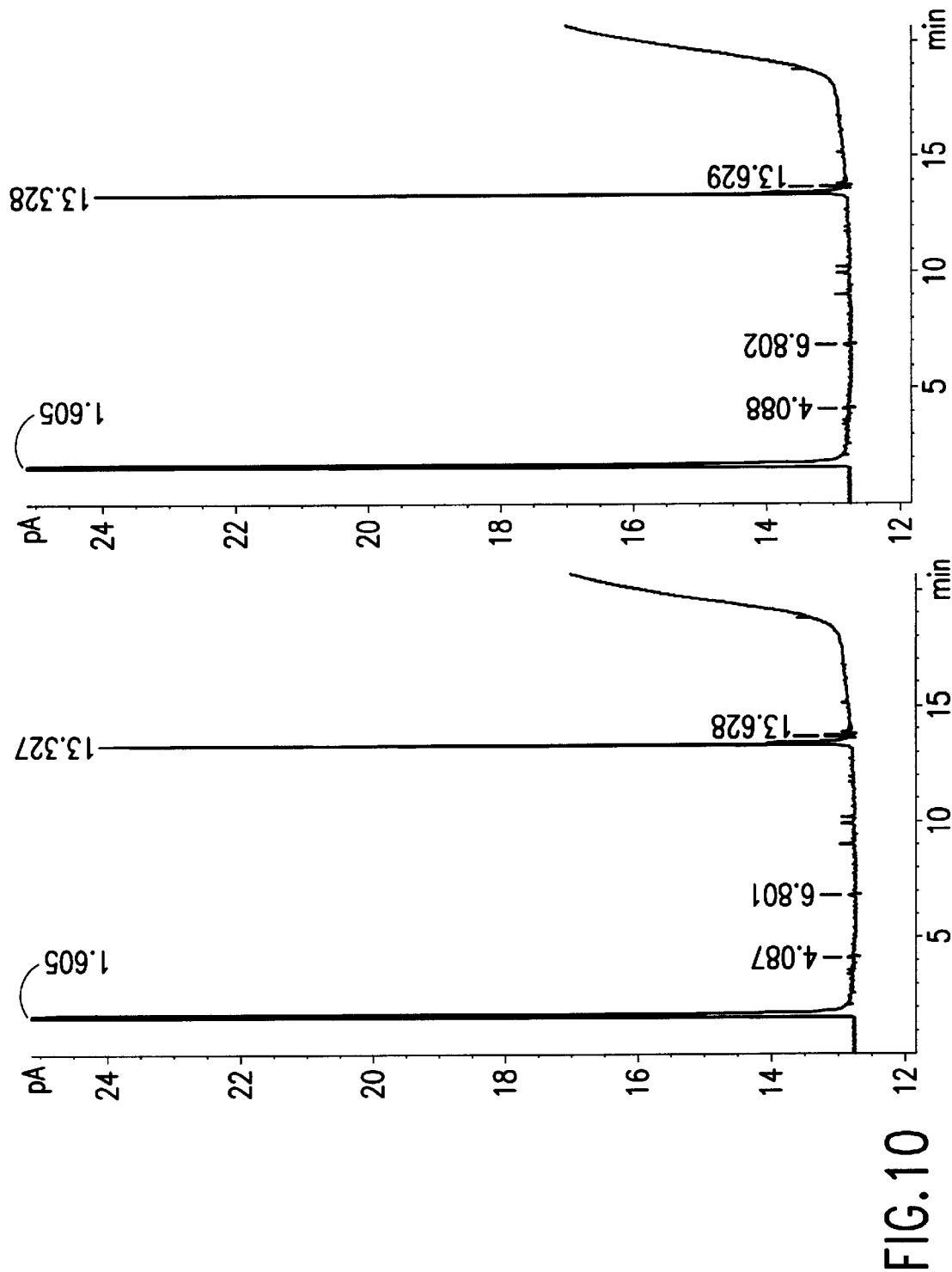
FIG. 10 shows the MIDI-FAME profile of RPS9.
Figure 11:
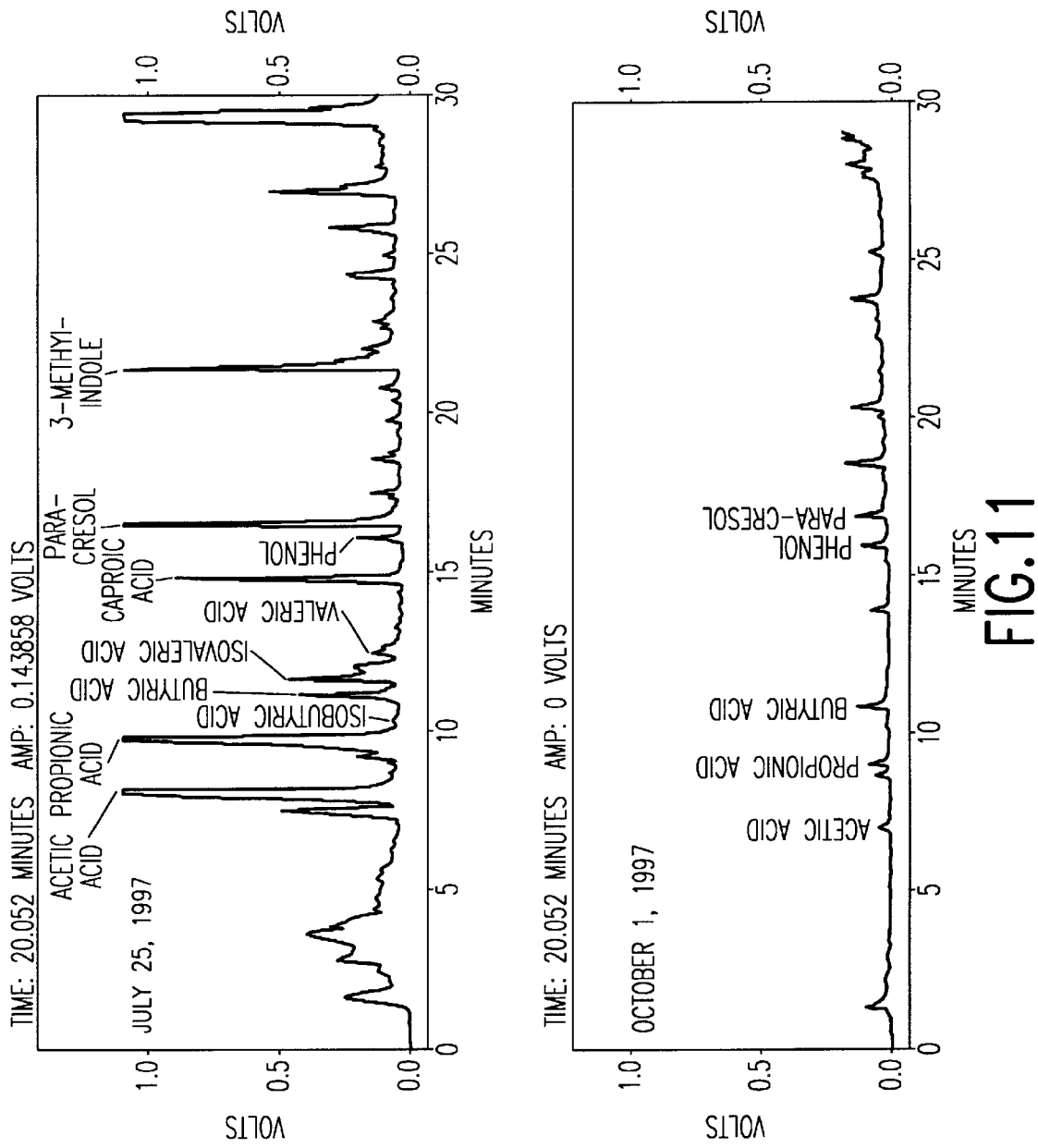
FIG. 11 shows chemical profiles of volatile compounds prior to (July 25) and following (October 1) the photosynthetic blooms in an anaerobic livestock waste lagoons.
Figure 12A:
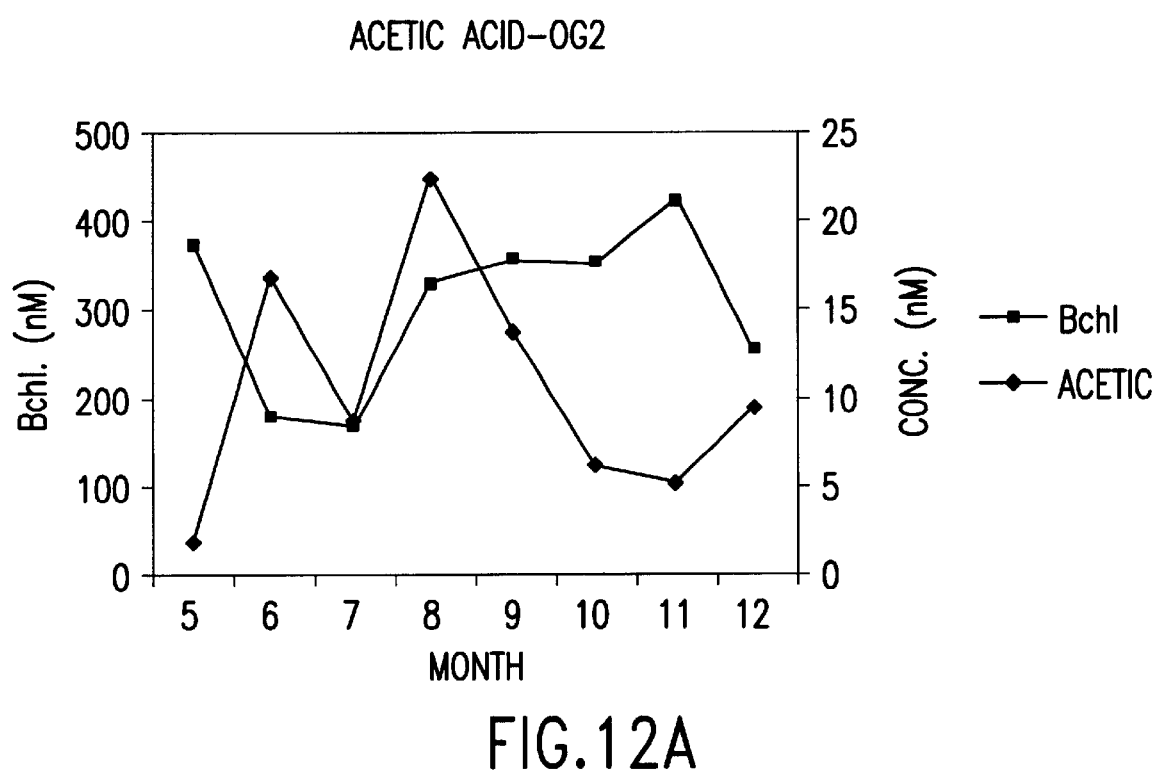
FIGS. 12A–G show fatty acid and Bchl profiles from an anaerobic livestock waste lagoons over an eight-month period.
Figure 12B:
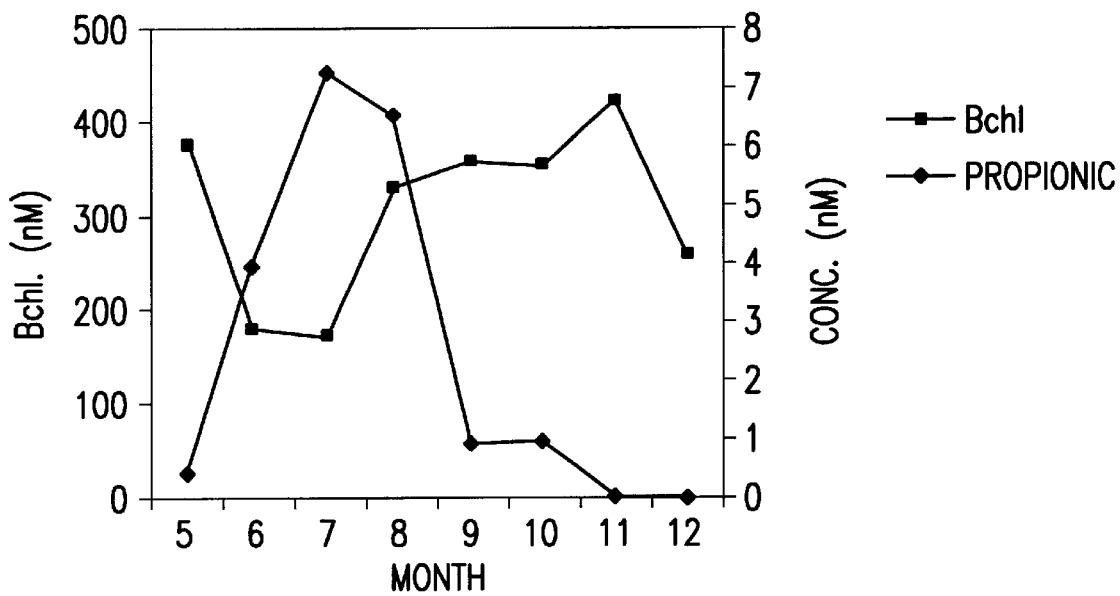
Figure 12C:
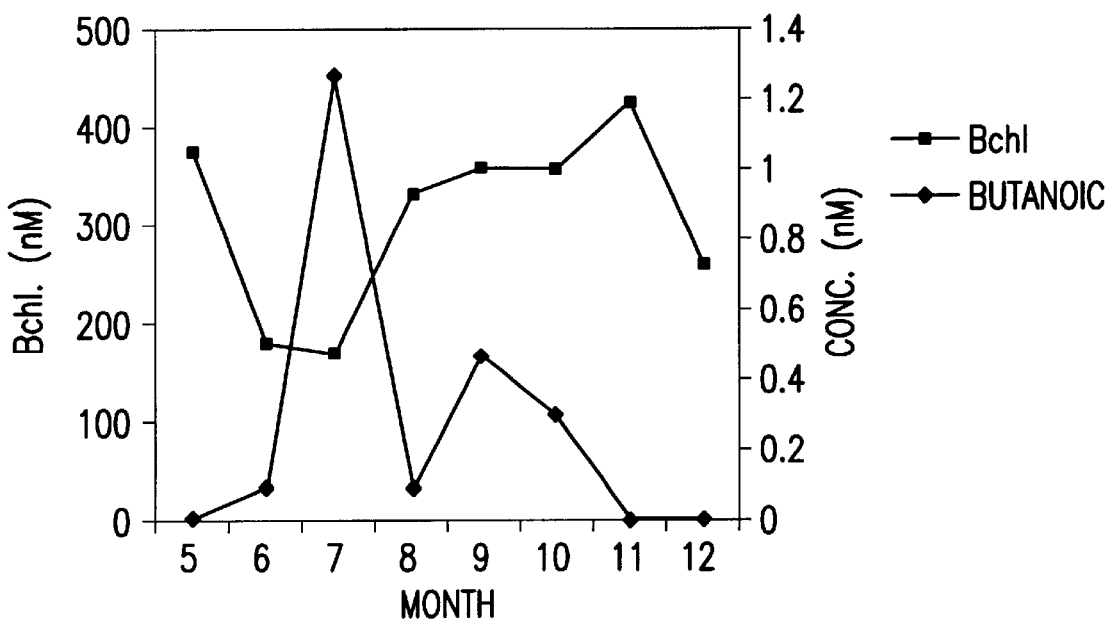
Figure 12D:
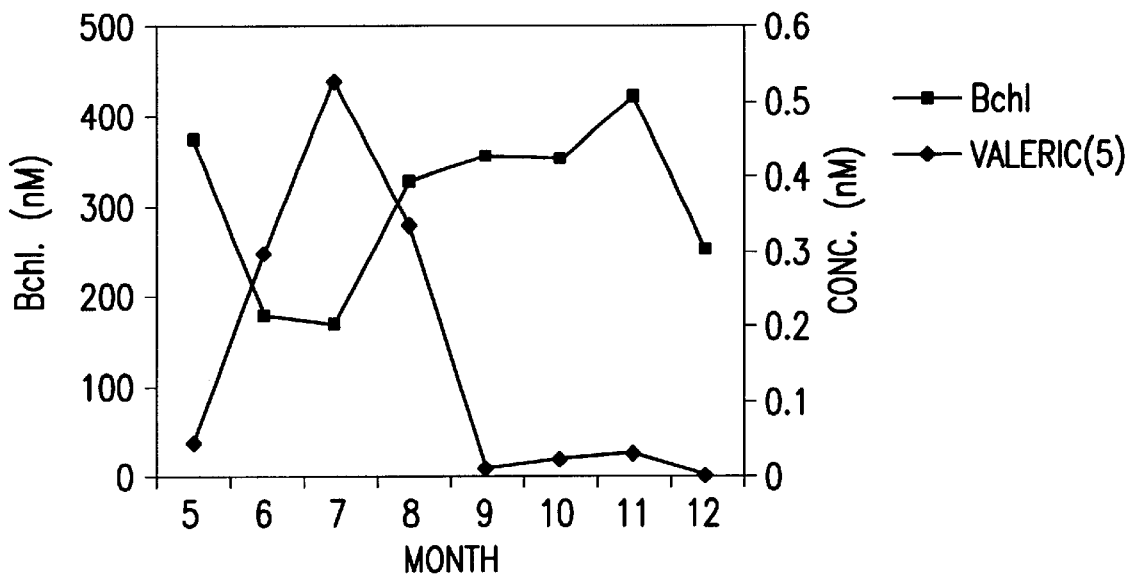
Figure 12E:
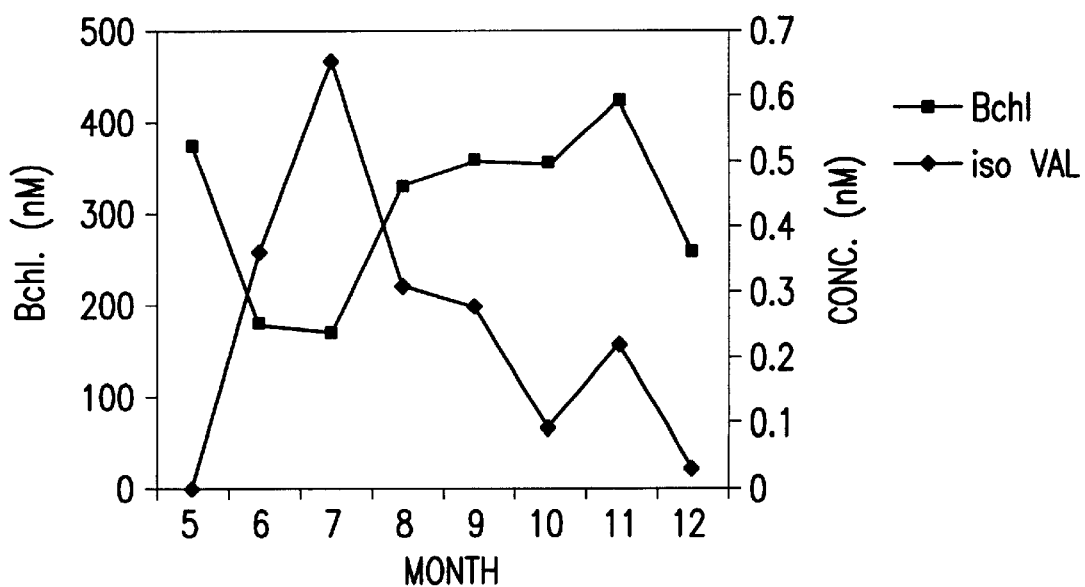
Figure 12F:
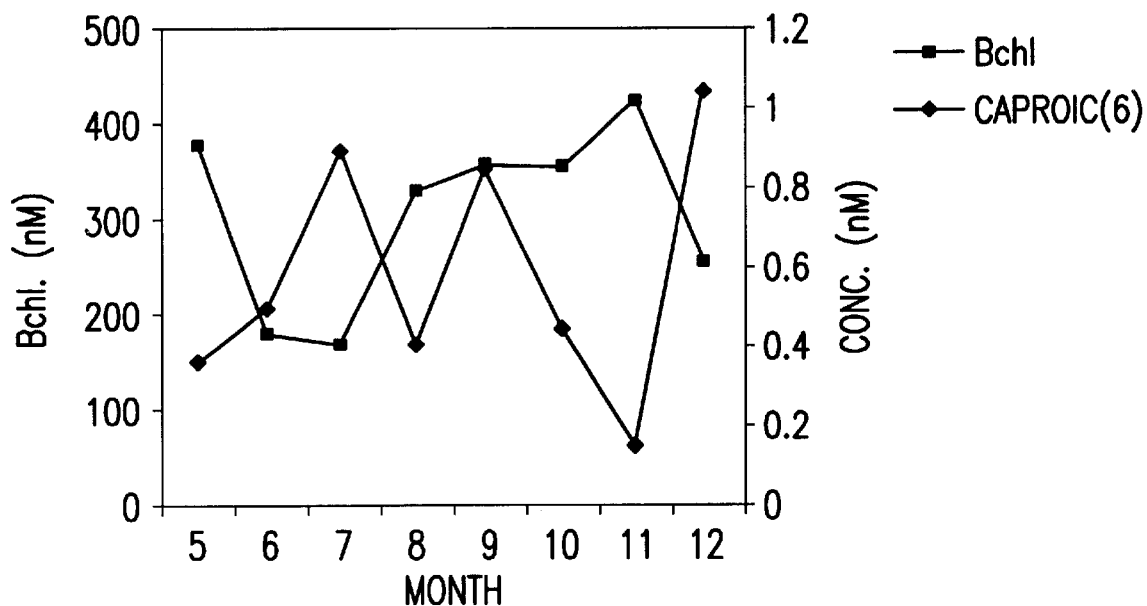
Figure 12G:
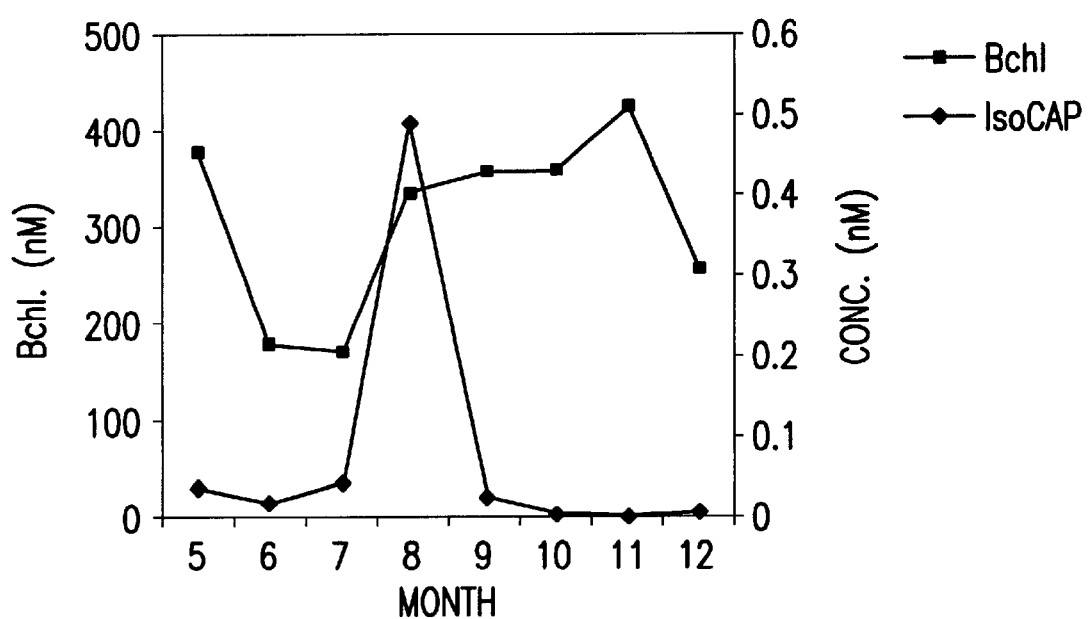
Figure 13A:
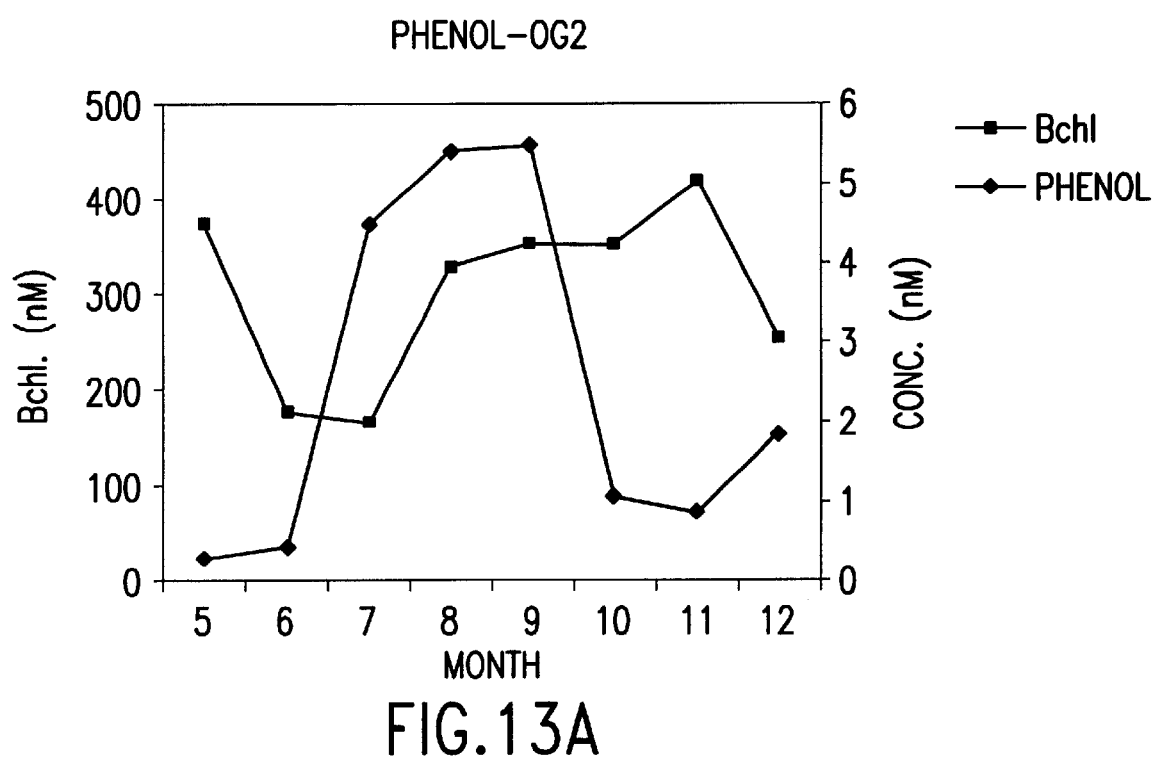
FIGS. 13A–E show aromatic and Bchl profiles from anaerobic livestock waste lagoons over an eight-month period.
Figure 13B:
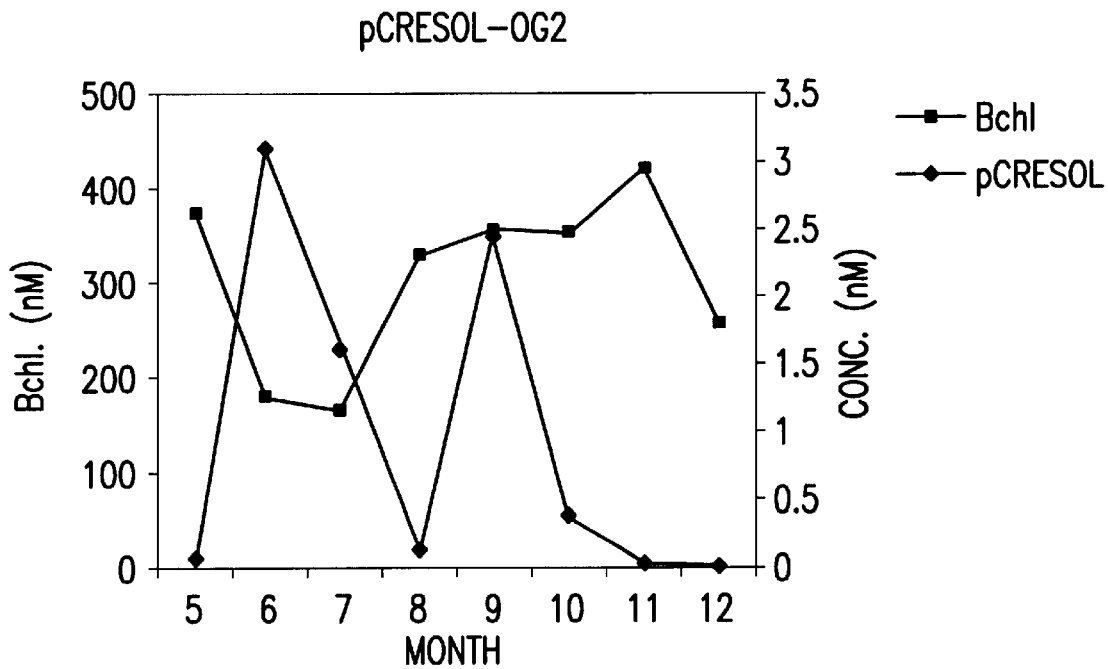
Figure 13C:
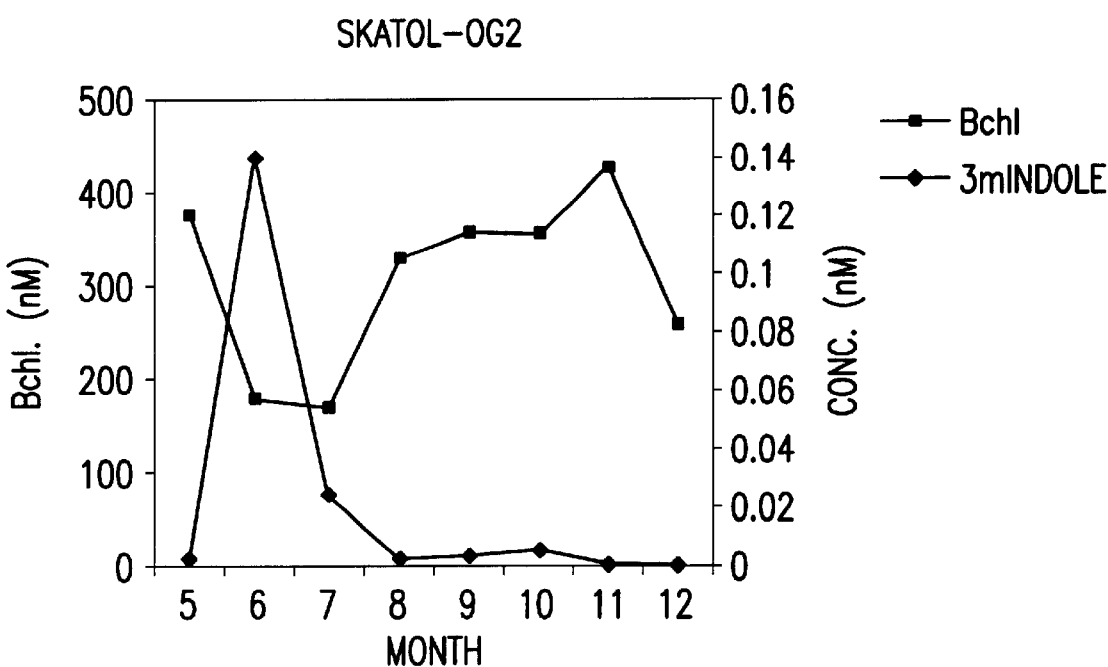
Figure 13D:
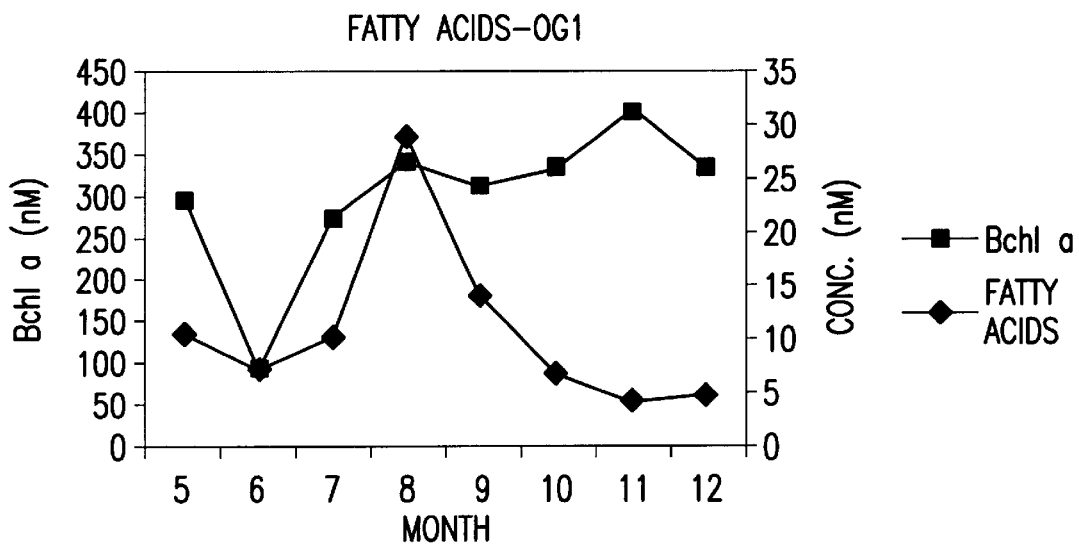
Figure 13E:
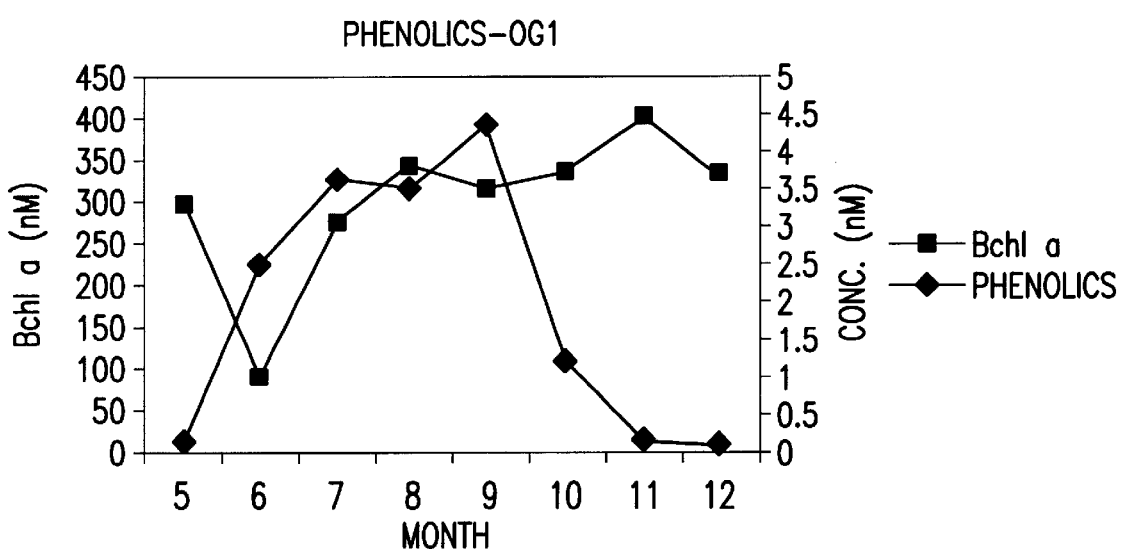

The major purple non-photosynthetic bacteria responsible for odor reduction was isolated from nine anaerobic swine waste lagoons in central Iowa, Colorado, Missouri, and North Carolina. Bacteriochlorophyll a profiles (FIG. 7), cell extract absorption spectra (FIG. 8), MIDI-FAME profiles (FIG. 10), morphology (FIG. 5), and a rRNA profile (FIG. 9) provided identifying characteristics of a new species. Physiological, morphological and genetic characterization identified the bacterial isolates as biotypes of a new strain of Rhodobacter, RPS9. RPS9 is phylogenetically close (98% identity) to *Rhodobacter azotoformans*, which was isolated from a human wastewater treatment system. The isolated strain is able to degrade the major volatile fatty acids and phenolic compounds of waste lagoons. The substrates utilized as reductants for RPS9 photosynthesis differ from other strains of Rhodobacter and reflect the environment in which it was isolated (Table 1).

TABLE 1

Photosynthetic electron donors and carbon sources used by species of the genus Rhodobacter. Donor/reductant sources for photosynthesis that are commonly observed in swine waste lagoons are designated in bold.

| Reductant | Growth | Reductant | Growth | Reductant | Growth |
|---|---|---|---|---|---|
| Acetate | + | Glutamate | − | Propionate | + |
| Arginine | + | Glycerol | + | Pyruvate | + |

TABLE 1-continued

Photosynthetic electron donors and carbon sources used by species of the genus Rhodobacter. Donor/reductant sources for photosynthesis that are commonly observed in swine waste lagoons are designated in bold.

| Reductant | Growth | Reductant | Growth | Reductant | Growth |
|---|---|---|---|---|---|
| Aspartate | − | Heptanoate | + | Propanol | + |
| Benzoate | − | Hydrogen/$CO_2$ | − | Propionate | + |
| Butyrate | + | Lactate | + | Pyruvate | + |
| Caproate | + | Malate | + | Sorbitol | + |
| Caproylate | − | Mannitol | + | Succinate | + |
| Citrate | − | Mannose | + | Sulfide/$CO_2$ | + |
| Ethanol | + | Methanol | + | Sulfur | |
| Formate | + | 3-Methyl Indole | + | Tartarate | + |
| Fructose | + | p-Cresol | + | Thiosul- | − |
| Fumarate | − | Pelargonate | − | fate/$CO_2$ | |
| Gluconate | − | Phenol | + | Valerate | + |
| Glucose | − | Propanol | + | | |

Figure 3:
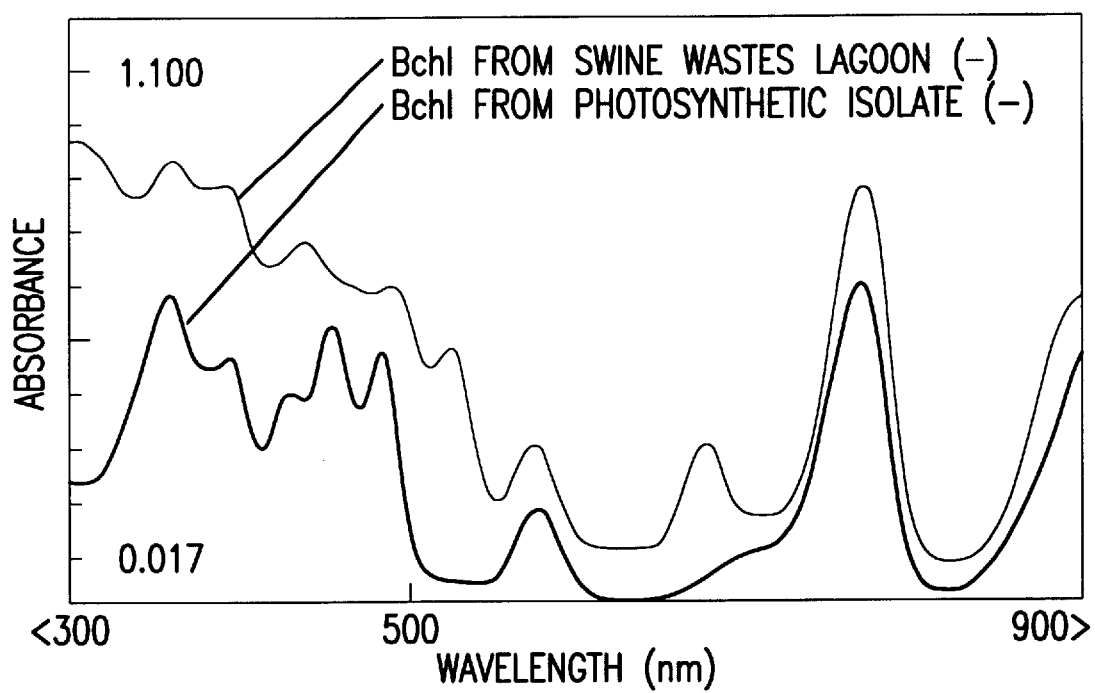
FIG. 3 shows the absorption spectra of bacteriochlorophyll α extracted from a purple anaerobic swine waste lagoon sample in Ogden, Iowa (top trace) and from RPS9.
Figure 4:
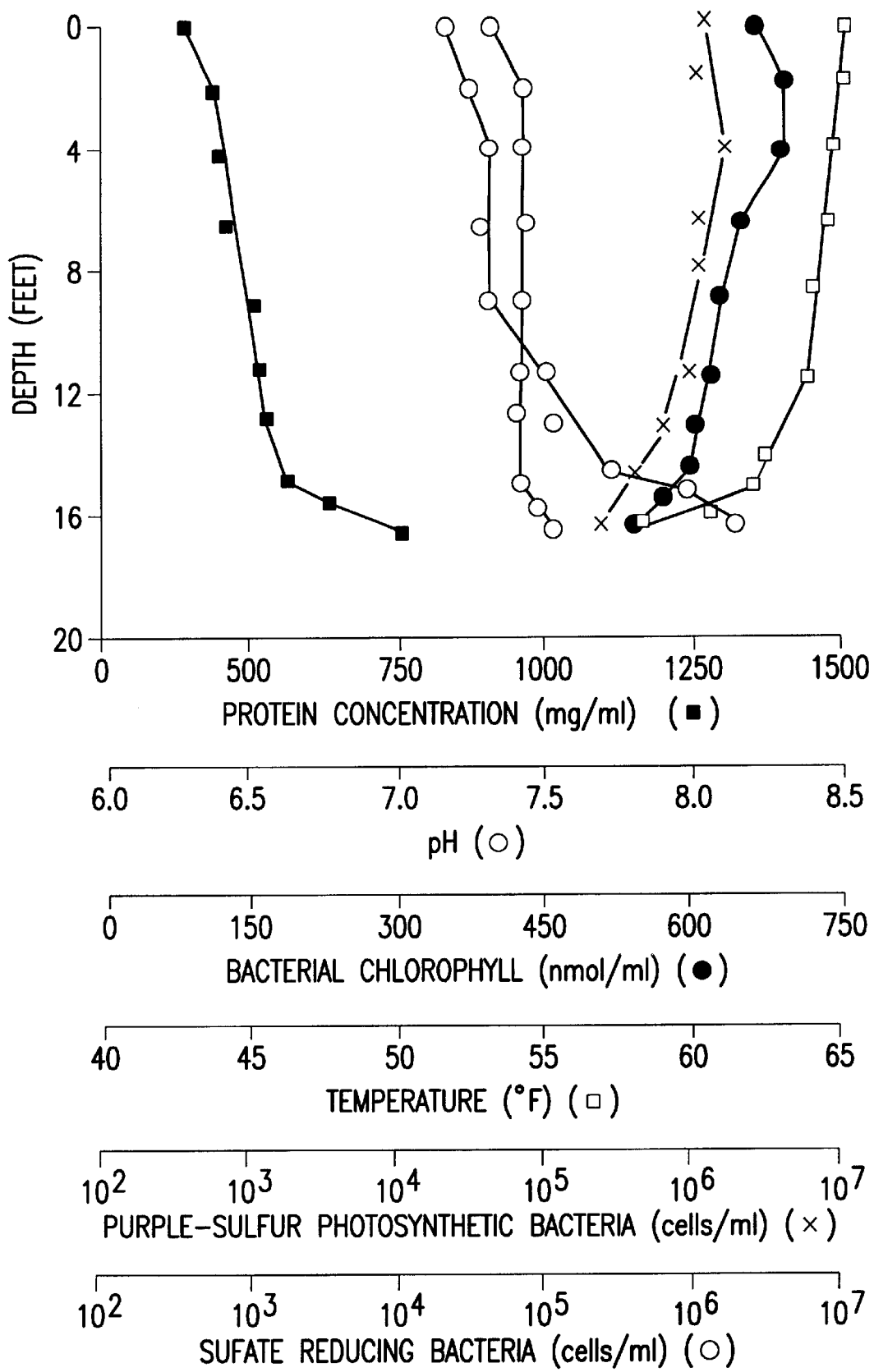
FIG. 4 shows the depth profile of temperature, pH, protein concentration, bacteriochlorophyll a concentration, population density of purple-sulfur photosynthetic bacteria, and sulfate reducing bacteria from an anaerobic livestock waste lagoon.

Bacteriochlorophyll α profiles, MIDI-FAME profiles, species specific rRNA hybridization, and cell extract absorption spectra show RPS9 to be the major photosynthetic bacteria in all the anaerobic swine waste lagoons tested. FIG. 3 shows the UV-visible absorption spectra of the chlorophyll extracted from a sample of lagoon material and from RPS9 and demonstrates that the major chlorophyll in RPS9, bacteriochlorophyll α, is also the major type of chlorophyll observed in all anaerobic swine lagoons tested. FIG. 8 shows cell extract absorption spectra for *Rhodobacter azotoformans* (a) and RPS9 (b). This observation has also been confirmed using rRNA-probes designed for RPS9 (FIG. 9) and by whole community fatty acid methyl ester (MIDI-FAME) (Table 1A, FIG. 10) (Sasser and Miler, 1997) profiles. The latter two techniques have also shown that during a photosynthetic bloom, RPS9 constitutes 40 to 50% of the microbial population in the anaerobic swine waste lagoons tested.

TABLE 1A

| MIDI-FAME | | | | | | | | |
|---|---|---|---|---|---|---|---|---|
| ID: 1885 | #3 970421 | | | | | Date of run: 23 APR 97 11:11:39 | | |
| Bottle: 3 RT | SAMPLE Area Ar/Ht Respon | | | [AEROBE] ECL Name | | # | Comment 1 | Comment 2 |
| 1.605 | 252778422 | 0.024 | | 7.039 | SOLVENT PEAK | | < min rt | |
| 4.087 | 1440 | 0.028 | 1.029 | 11.427 | 10:0 30H | 1.86 | ECL deviates 0.00 | |
| 6.801 | 2050 | 0.036 | | 13.817 | | | | |
| 13.327 | 75937 | 0.051 | 0.969 | 17.827 | Sum In Feature 7 | 92.43 | ECL deviates 0.002 | 18:1 w9c/w12t/w7c |
| 13.628 | 4684 | 0.049 | 0.968 | 18.000 | 18:0 | 5.71 | ECL deviates 0.000 | Reference 0.001 |
| ****** | 75837 | | | | SUMMED FEATURE 7 | 92.43 | 18:1 w7c/w9t/w12t 18:1 w12t/w9t/27c | 18:1 w9c/w12t/w7c |
| ****** | | | | | | | | |

| Solvent Ar | Total Area | Named Area | % Named | Total Amt. | Nbr Ref | ECL Deviation | Ref ECL shift |
|---|---|---|---|---|---|---|---|
| 252778422 | 84011 | 81962 | 97.56 | 79481 | 1 | 0.002 | 0.001 |

| | |
|---|---|
| TSBA [Rev 3.90] Rhodobacter | 0.758 |
| R. sphaeroides | 0.758 |
| R. capsulatus | 0.558 |
| Methylobacterium | 0.698 |
| | (48 h, *Pseudomonas mesophilica*) |

TABLE 1A-continued

MIDI-FAME

| | |
|---|---|
| M. mesophilicum* | 0.698 |
| | (48 h, Pseudomonas mesophilica) |
| M. radiotolorans | 0.644 |
| | (48 h, Pseudomonas radiora) |
| M. zatmanii | 0.549 |
| | (48 h) |
| Xanthobactor | 0.440 |
| X. flavus | 0.440 |
| CLIN [Rov 3.90] Methylobactorium | 0.399 |
| M. mesophilicum | 0.399 |
| Ochrobactrum | 0.355 |
| O. anthropi* | 0.355 |

To determine the physical and environmental parameters responsible for the photosynthetic bloom, we monitored the bacteriochlorophyll α concentration, volatile organic and inorganic emissions (Table 3), the chemical (protein, total nitrogen, total carbon and transition metals) composition and the meteorological conditions (air temperature, wind speed, solar radiation, relative humidity and wind direction) (Table 4) in both stages of an anaerobic swine waste lagoon through the years of 1997 and 1998 (Do 1998, 1999, Zahn 1997). Photosynthetic bloom was consistently observed (testing 15 lagoons in northern Missouri and four in central Iowa) to occur at lagoon temperatures between about 20° C. and 25° C. During photosynthetic blooms, concentrations of volatile organic compounds emitted from swine waste lagoon was dramatically decreased, with reductions of 93 to 98% for volatile fatty acids and 45 to 90% in aromatic compounds in the first stage of a two-stage lagoon following a thaw in May though December. (FIGS. 12 and 13).

TABLE 3

Average horizontal flux rate and average system flux rate for air pollutants collected over a 24 hr period from swine manure management systems described in Table 2.

| | Flux rate of analytes for individual swine waste storage systems | | | |
|---|---|---|---|---|
| Parameter | Type 1 | Type 2 | Type 3 | Type 4 |
| Mean wind velocity[s] (cm s.$^{-1}$) or ventilation rate[b] (m$^3$hr$^{-1}$) during sampling period | 110,000[b] | 190[a] | 128[a] | 90[a] |
| Ammonia flux rate (ng NH$_3$ cm$^{-2}$ s$^{-1}$) | 66† | 167 | 109 | 89 |

TABLE 2

Physical properties, elemental composition, and methane flux rates from 29 swine manure management systems in Iowa, Oklahoma, and North Carolina during the months of August and September, 1997. The range indicated for the parameters listed represents the standard error of the sample mean.

| | Site Classification‡ | | | |
|---|---|---|---|---|
| Parameter† | Type 1‡ | Type 2 | Type 3 | Type 4 |
| Site number (n) | n = 6 | n = 7 | n = 6 | n = 10 |
| Description of waste management system | DP; n = 5<br>PP; n = 1 | EB; n = 3<br>CLB; n = 3<br>ST; n = 1 | L; n = 6 | PL; n = 10 |
| System methane flux rate (g CH$_4$ system$^{-1}$ hr$^{-1}$) | 636 ± 47 | 1830 ± 148 | 13900 ± 760 | 11990 ± 540 |
| Volatile solids loading rate (kg VS day$^{-1}$ m$^{-m}$) | 79 ± 3.0 | 35 ± 2.6 | 0.3 ± 0.05 | 0.07 ± 0.02 |
| PH | 7.1 ± 0.04 | 7.3 ± 0.06 | 7.3 ± 0.06 | 7.1 ± 0.03 |
| Solid content (mg/ml) | 21.9 ± 0.9 | 13.4 ± 0.6 | 3.8 ± 0.4 | 2.8 ± 0.1 |
| % Carbon (% dry mass) | 37.2 ± 0.6 | 33.7 ± 0.5 | 16.6 ± 0.3 | 14.1 ± 0.3 |
| % Hydrogen (% dry mass) | 5.2 ± 0.3 | 4.9 ± 0.2 | 2.3 ± 0.2 | 1.8 ± 0.1 |
| % Nitrogen (% dry mass) | 3.0 ± 0.2 | 2.9 ± 0.2 | 1.8 ± 0.2 | 1.5 ± 0.1 |

†Instrumental error was <1% for CHN analysis and <0.1% for ICP-AES analysis.
‡Type 4 and Type 3 systems represent lagoon systems with and without anoxic photosynthetic blooms, respectively. Type 2 systems represent earthen, concrete, or steel-lined manure storage basins. Type 1 systems represent confinement buildings with short and long term, under-slat storage (pull-plug and deep-pit systems).
Sub-classification designations:
PL = phototrophic lagoon;
L = lagoon;
EB = earthen basin;
CLB = concrete-lined basin (outdoor);
ST = steel tank (outdoor);
DP = deep pit;
PP = pull-plug.

TABLE 3-continued

Average horizontal flux rate and average system flux rate for air pollutants collected over a 24 hr period from swine manure management systems described in Table 2.

| Parameter | Flux rate of analytes for individual swine waste storage systems | | | |
|---|---|---|---|---|
| | Type 1 | Type 2 | Type 3 | Type 4 |
| System Ammonia flux rate (g $NH_3$ system$^{-1}$ hr$^{-1}$) | 1060 | 1900 | 7700 | 6270 |
| Methane flux rate (ng $CH_4$ cm$^{-2}$ s$^{-1}$) | 34† | 178 | 218 | 200 |
| System methane flux rate (g $CH_4$ system$^{-1}$ hr$^{-1}$) | 550 | 2010 | 15410 | 14120 |
| Hydrogen sulfide flux rate (ng $H_2S$ cm$^{-2}$ s$^{-1}$) | 0.37† | 1.10 | 0.32 | 0.24 |
| System hydrogen sulfide flux rate (g $H_2S$ system$^{-1}$ hr$^{-1}$) | 5.9 | 12.5 | 22.7 | 16.9 |
| Priority pollutant (PP) flux rate (ng PP cm$^{-2}$ s$^{-1}$)‡ | 1.04† | 2.30 | 0.56 | 0.30 |
| System priority pollutant flux rate (g PP system$^{-1}$ hr$^{-1}$)‡ | 16.6 | 26.1 | 39.6 | 20.9 |
| Combined VOC flux rate (ng VOC cm$^{-2}$ s$^{-1}$) | 5.60† | 35.0 | 1.60 | 0.21 |
| System combined VOC flux rate (g VOC system$^{-1}$ hr$^{-1}$) | 89.9 | 394.0 | 113.1 | 14.5 |
| System total air pollutant flux rate (g TAP system$^{-1}$ hr$^{-1}$) | 1720 | 2420 | 15550 | 14150 |

†System flux rate calculated using an active surface area of 4,459,000 cm$^2$ and assume a homogenous emitting source for active surfaces.
‡U.S.-EPA priority pollutants identified in air samples: cresols (isomers and mixtures), hydrogen sulfide, phenol, and acetophenones.

Figure 6:
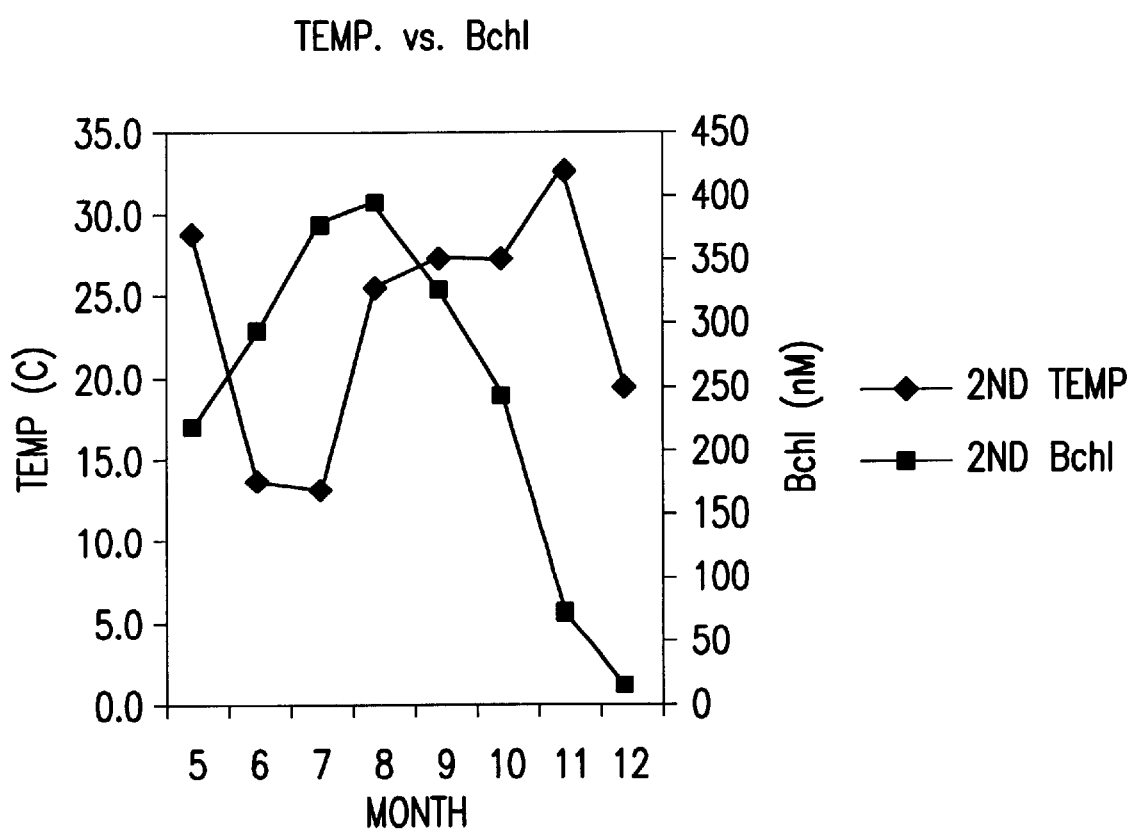
FIG. 6 shows the changes in bacteriochlorophyll in relation to sample temperatures in anaerobic livestock waste lagoons.

Bacteriochlorophyll α concentrations were initially high since the lagoon freezes before bacteriochlorophyll is degraded. (FIG. 6). As the lagoon warms in spring, microbial activity increases and the concentration of ammonia and volatile organic compounds emitted increases. (FIGS. 12A–G). When the lagoon temperature reaches 20 to 22° C. the concentration of bacterial chlorophyll increases and the concentration of VOCs decreases. (FIGS. 12A–G). In general, the concentration of volatile fatty acids decreased before the aromatic compounds. Compare FIGS. 12A–G with 13A–C. With the exception of hydrogen sulfide, similar graphs were observed with all of the organic and inorganic constituents known to contribute to the odors associated with swine wastes.

Similar graphs have also been generated using (1) rRNA profiles made using probes (FIG. 15) specific to RPS9 or (2) MIDI-FAME profiles (Table 1A, FIG. 10) to monitor the population levels of RPS9 instead of bacteriochlorophyll. According to bacterial chlorophyll, cell extract absorbance, MIDI-FAME, and 16S rRNA hybridization studies in the lagoon near Ogden, Iowa, RPS9 was the major photosynthetic bacterium responsible for the purple color and for odor reduction associated with the bloom. Of the physical, meteorological, and chemical variables tested, temperature, organic loading and pH were the major variables correlated with the appearance and timing of the photosynthetic bloom.

Accordingly, a first preferred embodiment of the invention, a purified bacterial culture of RPS9, and variants thereof, is provided having some or all of the identifying characteristics of ATCC (PTA3931). "Variants" refer to mutated, modified, or altered RPS9 cells having some or all of the identifying characteristics of RPS9 modified, altered, or mutated by chemical, genetic, radioactive or by any suitable method. Such variants and mutants of RPS9 and their progeny may be obtained in a variety of ways including the growth, use, mating, introduction of vectors or plasmids and/or other DNA fragments or segments, and/or mutagenic treatment of the bacterial cells (and those of their progeny). Identifying characteristics of this strain include, the bacteriochlorophyll a absorption profile of FIG. 7, cell extract absorption spectra of FIG. 8, the MIDI-FAME profile shown in Table 1A and FIG. 10, and the hybridization of the rRNA probe of FIG. 15(a) to the 16S rRNA sequence of FIG. 9. The bacteriochlorophyll a absorption spectra of FIG. 7 has absorption bands positioned at wavelengths of 771 nm, 574 nm, 394 nm and 358 nm. The cell extract absorption spectra of FIG. 8 distinguishes RPS9 (FIG. 8(a)) from Rhodobacter azotoformans (FIG. 8(b)). The MIDI-FAME profile shown in Table 1A and FIG. 10 identifies the major fatty acid 18:1 [Omega]7c[Omega]9c/[Omega]12c as a marker fatty acid for purple non-sulfur bacteria such as RPS9. The 16S rDNA sequence of FIG. 9 was detected by the rRNA probe of FIG. 15(a) demonstrating that RPS9 is a new species phylogenetically related to *Rhodobacter spherotides*.

According to another preferred embodiment of the invention, growth of RPS9 or variants thereof is enhanced in a livestock waste lagoon by adjusting the temperature, pH and organic load of the waste lagoon. The temperature of the lagoon is measured by any suitable method. In a preferred embodiment, temperature probes are lowered into the lagoon to obtain spot temperature measurements. A floating weather station may be used to collect temperature information. The temperature is preferably elevated to at least above about 22° C. The temperature may be adjusted by any suitable method including, e.g., increasing microbial activity, placing a transparent cover over the top of the lagoon, or transferring heat through pipes, liquid or air into the livestock waste lagoon. The temperature is preferably adjusted by increasing the microbial activity of the lagoon by adding an easily digestible carbohydrate. The pH may be measured using any suitable method, e.g., use of pH probes lowered into the lagoon. The pH is adjusted by titrating the lagoon with acid (e.g., HCl or acetic acid) or base (e.g., lime) to from about pH 6.9 to about pH 7.8. The pH may also be adjusted metabolically by providing a suitable substrate that will produce an acidic or basic metabolite. Organic load may be adjusted by diluting the lagoon with water, preferably such that the protein concentration of the livestock waste lagoon is less than about 1 gram of protein per liter of waste lagoon. Dilution of the lagoon with water results in a reduced organic load. Organic load may be measured by any suitable method, e.g., measuring dry protein weight, protein concentration, total carbon, or total nitrogen.

In another preferred embodiment, an inoculum comprising a biologically pure culture of RPS9 or variant thereof and a suitable carrier is used to innoculate a livestock waste lagoon and induce the growth of RPS9 in a livestock waste lagoon. Cultures are preferably grown in minimal salts media supplemented with VOC, amines, fatty acids and phenolic compounds for about 5 days at 22° C. Preferably, about 1 to about 5 mls of media (e.g., the media shown in Table 4) containng bacteria at a concentration of 2 mg cell protein/ml are provided directly to the livestock waste lagoon.

TABLE 4

Photosynthetic Mineral Salts Medium

Basic Medium (for 1 liter)

| | |
|---|---|
| Magnesium sulfate(heptahydrate), $MgSO_4.7H_2O$ | 0.33 g |
| Sodium chloroide, NaCl | 0.33 g |
| Ammonium chloride, $NH_4Cl$ | 0.5 g |
| Calcium chloride(dihydrate), $CaCl_2.2H_2O$ | 0.05 g |
| Sodium succinate | 0.3 g |
| Yeast extract | 0.02 g |
| Distilled water | 990 ml |
| pH 6.9 ± 0.1 | |
| After autoclaving, add the following separately filter sterilized solutions: | |
| Trace salts solution (see below) | 1.0 ml |
| Ferrous sulfate solution (200 mg $FeSO_4.7H_2O$ per liter) | 0.5 ml |
| Sodium bicarbonate solution (10 g $NaHCO_3$ per 100 ml) | 10.0 ml |
| Phosphate buffer solution (see below) | 10.0 ml |
| Trace Salts Solution | |
| Zinc sulfate(heptahydrate), $ZnSO_4.7H_2O$ | 10 mg |
| Manganese chloride(tetrahydrate), $MnCl_2.4H_2O$ | 3 mg |
| Boric acid, $H_3BO_3$ | 30 mg |
| Cobalt chloride(hexahydrate), $CoCl_2.6H_2O$ | 20 mg |
| Copper chloride(dihydrate), $CuCl_2.2H_2O$ | 1 mg |
| Nickel chloride(hexahydrate), $NiCl_2.6H_2O$ | 2 mg |
| Sodium molybdate, $NaMoO_4$ | 3 mg |
| Distilled water | 1000 ml |
| Phosphate Buffer Solution (for 1 liter) | |
| Potassium phosphate monobasic, $KH_2PO_4$ | 26 g |
| Sodium phosphate dibasic, $Na_2HPO_4$ | 33 g |
| Distilled water | 1000 ml |

Preparation The trace salts and phosphate buffer solutions can be stored for long period of time, but the ferrous sulfate and sodium bicarbonate solutions should be prepared fresh.
Enrichment The medium must be incubated anaerobically in the light. If the containers are not sealed, aerobic organisms will grow utilizing the succinate, a nonfermentable carbohydrate. The best light to use for incubation is either natural light (north window, to avoid excessive heating on sunny days) or tungsten lamps, at 25 cm distance if using a 25 watt bulb.
Reference: Phillips, J.A. and T.D. Brock. 1991. Laboratory Manual for Biology of Microorganisms, 6th ed. Prentice-Hall, Englewood Cliffs, NJ.

The cells are preferably cultured on the swine odor mixture shown in Table 5 as the sole electron and carbon source. The cells can be cultured on any of the carbon sources listed in table 1. However, use of the artificial swine odor mixture will result in the induction of the enzyme systems for the substrates normally present in anaerobic swine waste lagoons and is therefore preferred.

TABLE 5

Chemical composition of artificial swine odor.

| Analyte | Concentration Range (mM) | Analyte | Concentration Range (mM) |
|---|---|---|---|
| Dimethyl Disulfide | 0.2 | Acetic Acid | 16 |
| Propionic Acid | 3.5 | Isobutyric Acid | 1 |
| 2-Butanol | 0.8 | Butyric Acid | 2.4 |
| Isovaleric | 0.4 | Valeric Acid | 1 |
| Caproic Acid | 0.4 | Isocaroic Acid | 0.2 |
| Heptanoic Acid | 0.4 | Indole | 0.2 |
| 3-Methyl Indole | 0.4 | 4-Methyl Phenol | 0.4 |
| 4-Ethyl Phenol | 0.24 | Phenol | 0.4 |
| Benzyl Alcohol | 0.2 | Butylated Hydroxytoluene | 0.2 |
| Propionic acid | 0.4 | | |
| 2-Amino Acetophenone | 0.3 | Ammonium bicarbonate | 0.2 |
| | | Ammonium Acetate | 16 |

In a further preferred embodiment of the invention, a vector system is used to form a genetically-reconstituted RPS9 capable of producing a protein product. For example, a gene encoding a protein of interest is cloned into RPS9 using a suitable vector system. The vector preferably comprises a gene encoding the protein product, a promoter to regulate expression of the gene, and a selection gene to maintain the presence of the vector in the RPS9 cell. A preferred protein product is the enzyme cellulase. Other preferred protein products include xylanases, proteinase, lipases, and hemicellolases. A vector system that does not require the continual presence of antibiotic selection is preferred for expression of the protein product in RPS9. The use of a non-antibiotic based selection system avoids the need for continual addition of antibiotics to a large batch culture. An gene essential for the survival of the RPS9 is preferred as the selection gene. An especially preferred selection gene is the ffh gene of RPS9. Phillips, G. J. and T. J. Silhavy. (1992). The *E. coli* ffh gene is necessary for cell viability and efficient protein export. *Nature* 359: 744–6. The ffh gene complements a mutant knockout-strain of RPS9 that is missing a functional ffh gene. Mutation in this essential gene is used as a selectable marker for plasmid maintenance. The ffh gene is highly conserved and necessary for protein localization in bacteria. A preferred promoter is induced by adjusting the media in which the RPS9 are grown rather than by adding an exogenous compound. An especially preferred promoter sequence suitable for use in the present invention is the nifHDK promoter from *R. capsulatus* (D. Pollack, C. E. Bauer, and P. A. Scolnick, Gene 65, 269 (1988)) which is induced by placing RPS9 cells in a low ammonia media. The vector containing the gene of interest is transferred into the RPS9 strain by any gene transfer method suitable for gram-negative photosynthetic bacteria including conjugation, electroporation, as well as insertional mutagenesis. Other suitable vector systems for use in the invention include broad host range conjugational plasmids such as IncP, IncQ, Pbr322 and ColE1.

In another preferred embodiment, genetically reconstructed RPS9 cells are grown in a livestock waste lagoon and induced to produce a protein product. The cells are preferably removed from the waste lagoon and induced to express the protein product without the addition of an exogenous compound resulting in expression of the protein product. The system and method take advantage of the favorable conditions of the anaerobic livestock waste lagoon for growth of the RPS9 cells. The livestock waste and VOCs generated by the lagoon provide the necessary media for enhanced growth of the RPS9 cells. The plasmid vector system used to form the genetically reconstituted RPS9 cells does not require either the addition of antibiotics to maintain the plasmids in the cells or the addition of exogenous compounds to induce expression of the protein product. Protein product expression is preferably induced by removing the cells from the lagoon and placing them in a reduced ammonia media, e.g., (Table 6).

TABLE 6

Photosynthetic Mineral Salts Medium

Basic Medium for induction (for 1 liter)

| | |
|---|---|
| Magnesium sulfate(heptahydrate), $MgSO_4.7H_2O$ | 0.33 g |
| Sodium chloroide, NaCl | 0.33 g |
| Calcium chloride(dihydrate), $CaCl_2.2H_2O$ | 0.05 g |
| Sodium succinate | 0.3 g |
| Yeast extract | 0.02 g |
| Distilled water | 990 ml |
| pH 6.9 ± 0.1 | |

TABLE 6-continued

Photosynthetic Mineral Salts Medium

After autoclaving, add the following separately filter sterilized solutions:

| | |
|---|---|
| Trace salts solution (see below) | 1.0 ml |
| Ferrous sulfate solution (200 mg $FeSO_4.7H_2O$ per liter) | 0.5 ml |
| Sodium bicarbonate solution (10 g $NaHCO_3$ per 100 ml) | 10.0 ml |
| Phosphate buffer solution (see below) | 10.0 ml |

Trace Salts Solution

| | |
|---|---|
| Zinc sulfate(heptahydrate), $ZnSO_4.7H_2O$ | 10 mg |
| Manganese chloride(tetrahydrate), $MnCl_2.4H_2O$ | 3 mg |
| Boric acid, $H_3BO_3$ | 30 mg |
| Cobalt chloride(hexahydrate), $CoCl_2.6H_2O$ | 20 mg |
| Copper chloride(dihydrate), $CuCl_2.2H_2O$ | 1 mg |
| Nickel chloride(hexahydrate), $NiCl_2.6H_2O$ | 2 mg |
| Sodium molybdate, $NaMoO_4$ | 3 mg |
| Distilled water | 1000 ml |

Phosphate Buffer Solution (for 1 liter)

| | |
|---|---|
| Potassium phosphate monobasic, $KH_2PO_4$ | 26 g |
| Sodium phosphate dibasic, $Na_2HPO_4$ | 33 g |
| Distilled water | 1000 ml |

Figure 14:
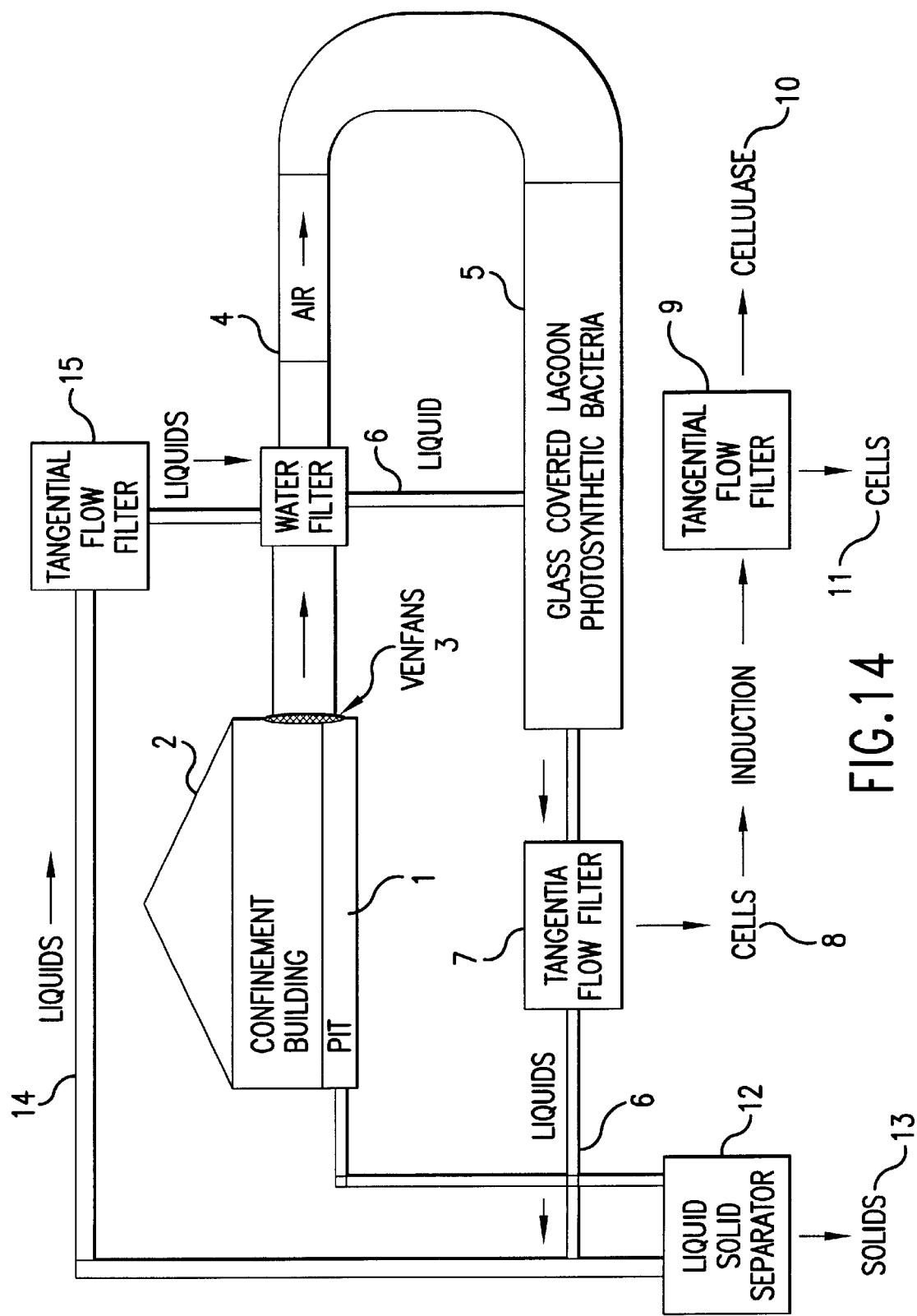
FIG. 14 depicts a preferred system for producing a protein product from genetically reconstituted RPS9 cells.

A preferred system for use in the invention is shown in FIG. 14. With reference to FIG. 14, livestock waste (liquid/solid mixture) is stored in a first stage pit 1 contained within a confinement building 2. The confinement building 2 is outfitted with ventilation fans 3 which draw air containing volatile organic compounds through water filter 4 to livestock waste lagoon 5. Water filter 4 comprises high velocity mists of water through which the exhausts from confinement building are funneled. High concentrations of VOCs build up within the confinement building 2 and are directed to the second stage comprising a covered livestock waste lagoon 5 to further stimulate bacterial growth. Liquid waste 6 from the pit 1 is transferred into livestock waste lagoon 5. RPS9 growth is enhanced in the livestock waste lagoon 5 by adjusting the temperature, pH and/or organic load in accordance with the present invention. Effluent from the livestock waste lagoon containing the genetically reconstituted RPS9 bacteria flows through a first tangential flow filter 7 to separate the RPS9 cells 8 from the liquid 6. Tangential flow filter 7 permits the RPS9 cells 8 to pass through the filter while the liquid 6 is recycled. The RPS9 cells 8 are induced to express a desired protein by washing the cells and placing them in a low ammonia media. The induced RPS9 cells produce the protein product (e.g., cellulase 10) and are directed through a second tangential flow filter 9 to separate the protein product 11 from the cells 11.

A liquid-solid separation phase is preferred to increase the stability and final yield of RPS9 in the photosynthetic lagoon. In the preferred liquid-solid separation phase, the liquid-solid mixture flows from pit 1 to a liquid-solid separator 12. Solids 13 are removed and liquid 14 flows through a third tangential flow filter 15 back into water filter 4 and livestock waste lagoon 5.

The first stage of the bioreactor system (i.e., pit 1 and confinement building 2) generates high concentration of volatile organic compounds, volatile solid, and ammonia/nitrogen. Swine wastes from type 1 storage systems, i.e. earthen basin, concrete-lined basin, steel tank (outdoor), or deep pit are preferred. Before addition to the second stage, the wastes are diluted using liquid runoff from the water filter 4. Initial dilutions are in a ratio of about 1 part waste from pit 1 to about 100 parts runoff water from water filter 4. Previous studies on photosynthetic lagoons have indicated that the organic load should be below about 3 g per liter dry weight.

It is to be understood that the application of the teachings of the present invention to a specific problem or environment will be within the capabilities of one having ordinary skill in the art in light of the teachings contained herein. Examples of the products of the present invention and processes for their use appear in the following examples.

EXAMPLE 1

ENHANCING GROWTH OF RPS9 IN A LIVESTOCK WASTE LAGOON

Growth of RPS9 was enhanced in an anaerobic livestock waste lagoon by adjusting the temperature, pH and organic load of the lagoon. The temperature of the waste lagoon was measured by lowering several temperature probes into the lagoon and recording the temperature. If the temperature was not at least about 22° C., glucose was added to increase microbial activity and raise the temperature. The pH of the livestock waste lagoon was measured by lowering several pH probes into the lagoon and recording the pH. If the pH was not from at least about pH 6.8 to about 7.1, the pH was adjusted by titration with an acid (i.e. HCl) or base (i.e. lime). The organic load of the livestock waste lagoon was measured by determining the protein concentration of the lagoon and diluting the lagoon with water as necessary to achieve an organic load of at least about 1 gram of protein per liter.

EXAMPLE 2

INNOCULATING A LIVESTOCK WASTE LAGOON WITH RPS9 TO REDUCE MALODEROUS VOCS

An inoculum comprising RPS9 and Photosynthetic Mineral Salts Medium (Table 4) at a concentration of 2 mg cell protein/ml was prepared. After adjusting the temperature, pH, and organic load as described in Example 1 above, 5 mls of innoculum was added to the livestock waste lagoon.

EXAMPLE 3

CLONING THE HYDRID CELLULASE GENES FROM THERMOMONOSPORA FUSCA AND PREVOTELLA RUMINICOLA INTO RPS9

The ffh gene of RPS9 is used as a selective marker to complement an ffh+ knockout RPS9 strain. PCR primers that are homologous to highly conserved regions of ffh and predominantly G+C are used to amplify a ffh region used as a hybridization probe to identify the ffh gene on a southern blot of RPS9 DNA. Using recombinant DNA techniques, a gene library representing DNA from a region of the Southern blot in the size range identified by the hybridization analysis is constructed. The ffh gene is isolated from the "mini-library" by colony hybridization. The resulting identified ffh gene is cloned into the broad host-range cloning vector pVK100. PVK100 is based on an RK2 plasmid replicon that is capable of autonomous replication in RPS9.

EXAMPLE 4

GENERATION OF AN FFH KNOCKOUT MUTATION OF RPS9

The plasmid insert DNA carrying the RPS9 ffh gene is characterized by DNA sequence analysis to identify the ffh coding region and subsequently subcloned using the polymerase chain reaction ("PCR") technique. The cloned ffh gene is converted to a mutant allele by replacement of an internal segment representing the coding region with a kanamycin antibiotic resistance marker from the transposon Tn5. Additional markers such as chloramphenicol or spectinomycin may also be used. This knockout allele of ffh is introduced into a RPS9 transformant carrying the cloned wild type ffh gene on the RK2 cloning vector by the following method: the ffh knockout allele is cloned into the "suicide" vector pGP704 and mated into RPS9 from *E. coli* with selection for kanamycin resistance. The pGP704-derivative plasmid cannot replicate in RPS9, and thus antibiotic resistant colonies will represent clones where the suicide vector has integrated into the bacterial chromosome by homology at the ffh locus. Kanamycin resistant colonies are screened to identify those that are also sensitive to ampicillin, the antibiotic encoded by pGP704. These clones represent those that have undergone a double recombination event where the genomic copy of ffh has been replaced by the knockout allele. The presence of the complementing copy of ffh demonstrates a knockout of the ffh gene. The ffh+-containing plasmid is maintained without antibiotic selection.

EXAMPLE 5

VECTOR SELECTION SYSTEM FOR EXPRESSION OF A GENETICALLY ENGINEERED CELLULASE

The ffh-based vector selection system is used to express a genetically engineered cellulase that was constructed by joining a carboxymethylcellulase (CMCase) enzymatic domain from *Prevotella ruminicola* with a cellulose-binding domain from the E2 cellulose-binding protein gene of *Thermomonospora fusca*. The product of this hybrid gene has increased enzymatic activity toward cellulose compared to the native CMCase from *P. ruminicola*. In order to express this gene in Rsp, a 1.5 kb gene fragment, encoding the 40.5 kd hybrid cellulase, is isolated from pGF7. The modified cellulase gene is placed under the control of the constitutively expressed kanamycin-resistance gene from Tn903, a promoter that is active in *R. sphaeroides*, prior to introduction into the RK2-based cloning vector. After introducing the cellulase construct to the ffh+vector the entire construct is introduced to the ffh mutant by displacing the resident complementing vector.

EXAMPLE 6

DETECTING THE PRESENCE OF RPS9 USING RIBOSOMAL RNA OLIGONUCLEOTIDES

A specific Rhodobacter PS9 probe has been designed and tested for the detection of quantification of RPS9. (FIG. 6B). The probe sequence (SEQ ID NO: 1) ACCATCTCTG-GAACCGCG hybridizes to RPS9 16S rDNA when probed at 45° C. The technique distinguishes RPS9 from closely related photosynthetic bacteria.

EXAMPLE 7

EXTRACTION OF RNA FROM MANURE/LAGOON SAMPLE

Direct Extraction of large scale RNA

The following was added to a small beaker (v=32ml): 10 g manure, 20 g 0.1 mm silica/zirconia, beads and 20 ml soil homoginization buffer (SHB; 4 M Guanidium Thiocyanate, 200 mM Sodium Phosphate pH 8.0, 25 mM Sodium Citrate, 0.5% Sarcosyl, 1.7% PVPP). The beads were beaten on ice 2 times for 1 minute with 2 minute breaks to allow for sample cooling. The manure slurry was decanted to sterile 50 ml tube on ice. The mixture was centrifuged at 3000×g for 5 minutes. The supernatent fluid was decanted into sterile 50 ml tube on ice. The soil pellet was resuspended in 10 ml SHB. Steps 4 and 5 were repeated and the supernatant fractions were pooled on ice. $\frac{1}{10}$v of 5M NaCl, and $\frac{1}{2}$v of 50% polyethylene glycole 8000 were added to the supernatant. The resulting fractions were mixed well and incubated on ice for 2 hours. The sample was centrifuged for 30 minutes at 4° C. at 12000×g. The supernatant fluid was discarded and the pellet was resuspended in 70% ethanol and centrifuged for 15 minutes at 4° C. at 12000 g. The ethanol was discarded and the pellet was resuspended in 2 ml of 120 mM Na-Phosphate buffer pH 7.2 plus 0.7 M NaCl. 1 ml of extract was added to two, 2 ml sterile tubes and combined with $\frac{1}{10}$v 10% CTAB solution. The solution was heated at 60° C. for 5–8 minutes. 0.7 ml phenol/CHCl$_3$/isoamyl alcohol (25/24/1) was added and the solution was equilibrated to pH 4.7 with 50 mM Na Acetate and mixed. The solution was centrifuged for five minutes at 15000×g and the aqueous phase was collected.

The pooled sample gently applied to the top of 1×3 cm HPT centrifuge column. The column was centrifuged at 100×g for 2 minutes or until sample was completely through the column. The sample was washed three times with 1 ml 120 mM Na$_2$HPO$_4$(pH 7.2) and placed in a 1.5 ml tube with cap removed under a syringe barrel. 1 ml of 300 mM K$_2$HPO$_4$ was added and the sample was eluted at 100×g for 4 minutes. The eluent from the HPT column was gently added to a packed Sephadex G75 spin column. A 1.5 ml tube was placed under the column and the column was centrifuged at 1400×g for 6 minutes at room temperature. The nucleic acids were precipitated overnight at −20° C. with $\frac{1}{10}$ volume 3M NaAcetate+0.6 v isopropanol. Resuspend in 200 μl DEPC H$_2$O.

CTAB is Hexadecyltrimethylammonium Bromide (Sigma H-6269) this compound is used to complex polysaccarides in nucleic acid extractions, and it also manages to remove some humic acid contamination from environmental samples.

DEPC is Diethylpyrocarbonate and is used to inactivate RNases in water used to make solutions for RNA extractions. Typically a 1% DEPC solution is left to stir overnight, and then autoclaved for approximately 45 minutes prior to use.

The above description and examples are only illustrative of preferred embodiments which achieve the objects, features, and advantages of the present invention, and it is not intended that the present invention be limited thereto. Any modifications of the present invention which come within the spirit and scope of the following claims is considered part of the present invention.

REFERENCES

Bernstein, H. D., M. A. Poritz, K. Strub, P. J. Hoben, S. Brenner and P. Walter. (1989). Model for signal sequence recognition from amino-acid sequence of 54K subunit of signal recognition particle. Nature 340: 482–6.

Blatny, J. M., T. Brautaset, H. C. Winther-Larsen, K. Haugan and S. Valla. (1997). Construction and use of a versatile set of broad-host-range cloning and expression vectors based on the RK2 replicon. *Appl Environ Microbiol* 63: 370–9.

de Lorenzo, V. (1992). Genetic engineering strategies for environmental applications. *Curr Opin Biotechnol.* 3: 227–321.1.

DiSpirito, A. A., Y. S. Do, C. L. Krema, J. Emerson, and Zahn, J. A. 1995. Methods to monitor microbial populations and odors from livestock wastes, In Proceedings of the international livestock odor conference. pp. 80–85. Iowa State University College of Agriculture. Ames, Iowa.

DiSpirito, A. A., Y. S. Do, C. L. Krema, and J. A. Zahn. 1996. Methods to Monitor Odors from Livestock Wastes. pp. 395–400. In Proceedings of American Association of Swine Practitioners.

DiSpirito, A. A. and J. A. Zahn. 1998. *Device for Quantitation of Odors from Liquid Livestock Wastes.* Pat. No. 5,766,551. United States Patent and Trademark Office. Washington, DC.

DiSpirito, A. A. and J. A. Zahn. 1999. *Methods and Means for Quantitation of Odors from Livestock Wastes.* Pat. No. 5,898,003. United States Patent and Trademark Office. Washington, D.C.

Do, T. S., J. A. Zahn, L. Merrill, L. Halverson, J. McKinney and A. A. DiSpirito. 1997. Odor remediation in anaerobic livestock waste lagoons using phototrophic bacteria. Abstract Abstract Q-7. p. 423General Meeting American Society for Microbiology.

Do, T. S., D. H. Buckley, T. M. Schmidt, and A. A. DiSpirito. 1999. Isolation and characterizations of a new species of Rhodobacter, RPS9, and their role in odor remediation in anaerobic swine waste lagoons. Abstract Q284, p. 587. General Meeting American Society for Microbiology.

Donohue, T. J. and S. Kaplan. (1991). Genetic techniques in Rhodospirillaceae. *Methods Enzymol.* 204: 459–485.

Dravnieks, Andrew. 1985. Atlas of odor character profile. American Society for Testing and Materials, Philadelphia, Pa.

Gibson, J. and C. S. Harwood. 1995. Degradation of aromatic compounds by nonsuolfur purple bacteria. In. R. E. Blankenship, M. T. Madigan and C. E. Bauer (eds.): Anoxygenic Photosynthetic Bacteria, pp. 991–1003. Kluwer Academic Pub. Boston, Mass.

Gottschalk, G. 1988. Bacterial metabolism: Second edition. Springer-Verlag Publishers, New York.

Harayama, S., R. A. Leppik, M. Rekik, N. Mermod, P. R. Lehrbach, W. Reineke and K. N. Timmis. (1986). Gene order of the TOL catabolic plasmid upper pathway operon and oxidation of both toluene and benzyl alcohol by the xylA product. *J Bacteriol* 167: 455–61.

Hobbs, P. J., T. H. Misselbrook, and B. F. Pain. 1995. Assessment of odours from livestock wastes by a photoionization detector, an electronic nose, olfactometry and gas chromatography-mass spectrometry. J. Agric. Engng. Res. 60:137–144.

Japenga, J. J., and Harmsen, K. 1990. Determination of mass balances and ionic balances in animal manure. Netherlands J. Agric. Sci. 38:353–367.

Jensen, M. T., R. P Cox, and B. B. Jensen. 1995. 3-Methylindole and indole produciton by mixed populations of pig fecal bacteria. Appl. Environ. Microbiol. 61(8): 3180–3184.

Jones, D. D., D. Ess, and T. Menke. 1997. Manure storage systems and treatment alternatives. In Kelly McGuire (ed.) Envirionmental assurance program. National Pork Producers Council. Des Moines, Iowa.

Imhoff, F. J., 1995. In. R. E. Blankenship, M. T. Madigan and C. E. Bauer (eds.): Anoygenic Photosynthetic Bacteria, pp. 1–15. Kluwer Academic Pub., Boston, Mass.

Kobayashi, M. and M. Kobayashi. 1995. Waste remediation and treatment using anoxygenic phototrophic bacteria. In. R. E. Blankenship, M. T. Madigan and C. E. Bauer (eds.): Anoxygenic Photosynthetic Bacteria, pp. 991–1003. Kluwer Academic Pub. Boston, Mass.

Lana, R. P., J. B. Russell, M. E. Amburgh. 1998. The role of pH in regulating ruminal methane and ammonia production. J. Anim. Sci. 76:2190–2196.

Letson, D., and Gollehon, N. 1996. Confined animal production and the manure problem. Choices. 11(3):18–24.

Liden, E., S. Nordin, L. Hogman, A. Ulander, F. Deniz, and A. G. Gunnarsson. 1998. Assessment of odor annoyance and its relationship to stimulus concentration and odor intensity. Chem. Senses. 23:113–117.

Livermore, A. and D. G. Laing. 1998. The influence of chemical complexity on the perception of multicomponent odor mixtures. Perception and psychophysics. 60(4): 650–661.

Mackie, R. I., P. G. Stroot, and V. H. Varel. 1998. Biochemical identification and biological origin of key odor components in livestock waste. J. Anim. Sci. 76:1331–1342.

Maglione, G., O. Matsushita, J. B. Russell and D. B. Wilson. (1992). Properties of a genetically reconstructed Prevotella ruminicola endoglucanase. *Appl Environ Microbiol* 58: 3593–7.

Majewski, M. S. 1990. Field methods comparisons for estimating evaporative flux densities of pesticides from fallow soil. Order number 9110651. UMI Dissertation Services. Ann Arbor, Mich.

Miller, V. L. and J. J. Mekalanos. (1988). A novel suicide vector and its use in construction of insertion mutations: osmoregulation of outer membrane proteins and virulence determinants in *Vibrio cholerae* requires toxR. *j Bacteriol.* 170: 2575–2583.

Miner, J. R. 1982. Controlling odors from livestock production facilities. pp. 30–35. In R. J. Smith (ed.) Research results in manure digestion, runoff, refeeding, odors. North central regional research publication no. 284. Ames, Iowa.

Miner, J. R. 1995. An executive summary: A review on the literature on the nature and control of odors from pork production facilities. National Pork Producers Council. Des Moines, IAphillips, J. A. and T. D. Brock. 1991. Laboratory mannual for biology of microorganisms, 6$^{th}$ ed., Prentice Hall, Englewood Cliffs, N.J.

Phillips, G. J. and T. J. Silhavy. (1992). The *E. coli* ffh gene is necessary for viability and efficient protein export. *Nature* 359: 744–6.

Prentki, P. and H. M. Krisch. (1984). In vitro insertional mutagenesis with a selectable DNA fragment. *Gene* 29: 303–313.

Reece, K. R. and G. J. Phillips. (1995). New plasmids carrying antibiotic-resistance cassettes. *Gene* 165: 141–142.

Romisch, K., J. Webb, J. Herz, S. Prehn, F. Frank, M. Vingron and B. Dobberstein. (1989). Homology of 54K protein of signal-recognition particle, docking protein and two *E. coli* proteins with putative GTP-binding domains. *Nature* 340: 478–82.

Sambrook, J., E. F. Fritsch and T. Maniatis (1989). *Molecular cloning a laboratory manual.* Cold Spring Harbor, N.Y., Cold Spring Harbor Press.

Siefert, E., R. L. Irgens, and N. Pfennig. 1978. Phototrophic purple and green bacteria in a sewage treatment plant. Appl. Environ. Microbiol. 35:38–44.

Sievers, D. M., and Iannotti, E. L. 1982. Anaerobic processes for stabilization and gas production. p. 1–10. In R. J. Smith (ed.) Research results in manure digestion, runoff, refeeding, odors. North central regional res. Publ. 284. North Central Regional Res., Ames, Iowa.

Sirevaag, R. 1995. Carbon metabolism in green bacteria. In. R. E. Blankenship, M. T. Madigan and C. E. Bauer (eds.): Anoxygenic Photosynthetic Bacteria, pp. 991–1003. Kluwer Academic Pub. Boston, Mass.

Thauer, R. K. 1989. pp. 205–248. In. Autotrophic bacteria. H. G. Schlegel and B. Bowien. eds. Springer-Verlag, New York.

Tindall, J. and W. D. Grant. 1986. pp. 101–156. In. Anaerobic bacteria in habitats other than man. E. M. Barenas and G. C. Mead (eds.). Blackenwell Scientific Publications, Boston.

van Gemerden, H. and H. H. Beeftink. 1983. In Studies in Microbiology Vol. 4, The phototrophic bacteria: Anaerobic life in the light. (J. G. Ormerod, ed.) pp 146–185. University of California Press, Los Angeles.

Wolfe, R. S. 1996. 1776–1996: Alessandro Volta's combustible air. Am. Soc. for Microbiol. News 62(10):529–534.

Zahn, J. A., J. L. Hatfield, Y. S. Do, A. A. DiSpirito, D. A. Laird, and R. L. Pfeiffer. 1997. Characterization of volatile organic emissions and wastes from a swine production facility. J. Environ. Qual. 26: 1687–1696.

Zahn, J. A. 1997. Swine odor and emissions from pork production. pp. 20–122, In Kelly McGuire (ed.) Environmental assurance program. National Pork Producers Council. Des Moines, Iowa.

What is claimed as new and desired to be protected by Letters Patent of the United States is:

1. A biologically pure culture of a Rhodabacter PS9 strain deposited under the number ATCC (PTA-3931) and mutants thereof wherein said mutants are capable of utilizing 3-methyl indole as a carbon and electron source.

2. The Rhodabacter PS9 strain of claim 1 wherein said strain is detected by hybridizing the rRNA probe of FIG. 15a (SEQ ID NO: 1) to the 16S rDNA sequence of said strain.

3. An inoculum comprising the culture of claim 1 and a carrier.

4. The inoculum of claim 3 wherein said carrier comprises media.

5. The Rhodobacter PS9 strain of claim 1 wherein said strain is capable of degrading malodorous volatile organic compounds.

6. The Rhodobacter PS9 strain of claim 1 wherein said strain is capable of degrading fatty acids and phenolic compounds.

7. The Rhodobacter PS9 strain of claim 1 wherein said strain is capable of degrading fatty acids selected from the group consisting of butanoic acid, pentanoic acid, hexanoic acid and heptanoic acid.

8. The Rhodobacter PS9 strain of claim 1 wherein said strain is capable of degrading phenolic compounds selected from the group consisting of phenol and para-cresol.

9. A method for inoculating a livestock waste lagoon with the innoculum of claim 3 comprising:

adjusting the organic load of the waste lagoon wherein the protein concentration of the livestock waste lagoon is less than about 1 gram per liter;

elevating the temperature of said livestock waste lagoon to at least about 22° C.;

adjusting the pH of said livestock waste lagoon to from about pH 6.9 to about 7.8; and providing said innoculum to said waste lagoon.

10. The Rhodobacter PS9 strain of claim 1 further comprising a vector.

11. The Rhodobacter PS9 strain of claim 10 wherein said vector comprises a selection gene, a gene encoding a protein product and a promoter for regulating expression of said protein product.

12. The Rhodobacter PS9 strain of claim 11 wherein said selection gene is fifty four homologue (ffh).

13. The Rhodobacter PS9 strain of claim 11 wherein said protein product is encoded by a cellulase gene.

14. The Rhodobacter PS9 strain of claim 11 wherein said promoter is nifHDK.

15. The Rhodobacter PS9 strain of claim 11 wherein said vector does not require the presence of antibiotics to maintain said vector in said Rhodobacter PS9 strain.

16. The Rhodobacter PS9 strain of claim 11 wherein inducing expression of said promoter does not require the addition of an exogenous compound.

* * * * *

UNITED STATES PATENT AND TRADEMARK OFFICE
CERTIFICATE OF CORRECTION

PATENT NO. : 6,489,156 B1
DATED : December 3, 2002
INVENTOR(S) : Alan A. Dispirito et al.

It is certified that error appears in the above-identified patent and that said Letters Patent is hereby corrected as shown below:

Column 2,
Line 49, under the heading "SUMMARY OF THE INVENTION" the letter "α" should be changed to -- *a* --.

Column 3,
Lines 56, under the heading "BRIEF DESCRIPTION OF THE DRAWINGS" the letter "α" should be changed to -- *a* --.
Line 58, under the heading "BRIEF DESCRIPTION OF THE DRAWINGS" the letter "a" should be changed to -- *a* --.

Column 5,
Line 15, under the heading "DETAILED DESCRIPTION OF PREFERRED EMBODIMENTS" the letter "a" should be changed to -- *a* --.

Column 6,
Line 14, under the heading "DETAILED DESCRIPTION OF PREFERRED EMBODIMENTS" the word "Sulfur  " should be changed to -- Sulfur - --.
Lines 20 and 27, under the heading "DETAILED DESCRIPTION OF PREFERRED EMBODIMENTS" the letter "α" should be changed to -- *a* --.

Column 7,
Line 19, under the heading "DETAILED DESCRIPTION OF PREFERRED EMBODIMENTS" the letter "α" should be changed to -- *a* --.

Column 9,
Line 37, under the heading "DETAILED DESCRIPTION OF PREFERRED EMBODIMENTS" the letter "α" should be changed to -- *a* --.

Column 10,
Lines 9 and 13, under the heading "DETAILED DESCRIPTION OF PREFERRED EMBODIMENTS" the letter "a" should be changed to -- *a* --.

UNITED STATES PATENT AND TRADEMARK OFFICE
CERTIFICATE OF CORRECTION

PATENT NO. : 6,489,156 B1
DATED : December 3, 2002
INVENTOR(S) : Alan A. Dispirito et al.

It is certified that error appears in the above-identified patent and that said Letters Patent is hereby corrected as shown below:

Column 14,
Line 17, under the heading "EXAMPLE 1, ENHANCING GROWTH OF RPS9 IN A LIVESTOCK WASTE LAGOON" the letter "C.," should be changed to -- C, --.

Column 23,
Line 22, the letter "C.;" should be changed to -- C --.

Signed and Sealed this

Eleventh Day of March, 2003

JAMES E. ROGAN
*Director of the United States Patent and Trademark Office*